US009522970B2

(12) United States Patent
Koltzenburg et al.

(10) Patent No.: US 9,522,970 B2
(45) Date of Patent: Dec. 20, 2016

(54) COMB POLYMERS AND USE THEREOF FOR THE PRODUCTION OF ACTIVE OR EFFECTIVE INGREDIENT FORMULATIONS

(75) Inventors: Sebastian Koltzenburg, Dannstadt-Schauernheim (DE); Peter Dombo, Wiesbaden (DE); Günter Oetter, Frankenthal (DE); Matthias Bratz, Maxdorf (DE)

(73) Assignee: BASF SE, Ludwigshafen (DE)

( * ) Notice: Subject to any disclaimer, the term of this patent is extended or adjusted under 35 U.S.C. 154(b) by 180 days.

(21) Appl. No.: 12/443,921

(22) PCT Filed: Oct. 4, 2007

(86) PCT No.: PCT/EP2007/060553
§ 371 (c)(1),
(2), (4) Date: Apr. 1, 2009

(87) PCT Pub. No.: WO2008/040786
PCT Pub. Date: Apr. 10, 2008

(65) Prior Publication Data
US 2010/0048655 A1    Feb. 25, 2010

(30) Foreign Application Priority Data

Oct. 5, 2006  (EP) .................................... 06121851

(51) Int. Cl.
| | |
|---|---|
| A01N 43/64 | (2006.01) |
| A61K 31/41 | (2006.01) |
| C08F 220/26 | (2006.01) |
| A01N 25/10 | (2006.01) |
| A01N 25/30 | (2006.01) |
| A61K 8/86 | (2006.01) |
| A61Q 19/00 | (2006.01) |
| C08F 220/14 | (2006.01) |
| C08F 226/10 | (2006.01) |
| C08F 265/00 | (2006.01) |
| C08F 265/04 | (2006.01) |
| C08F 283/06 | (2006.01) |
| C08F 290/00 | (2006.01) |
| C08F 290/06 | (2006.01) |
| C08L 51/00 | (2006.01) |
| C08L 53/00 | (2006.01) |
| C08F 220/18 | (2006.01) |

(52) U.S. Cl.
CPC ............. *C08F 220/26* (2013.01); *A01N 25/10* (2013.01); *A01N 25/30* (2013.01); *A61K 8/86* (2013.01); *A61Q 19/00* (2013.01); *C08F 220/14* (2013.01); *C08F 226/10* (2013.01); *C08F 265/00* (2013.01); *C08F 265/04* (2013.01); *C08F 283/06* (2013.01); *C08F 290/00* (2013.01); *C08F 290/06* (2013.01); *C08F 290/062* (2013.01); *C08L 51/003* (2013.01); *C08L 53/00* (2013.01); *C08F 2220/1883* (2013.01)

(58) Field of Classification Search
CPC ........ A01N 25/30; A01N 37/50; A01N 43/40; A01N 43/56; A01N 43/653; A01N 43/90; A01N 25/10; C08F 220/14; C08F 220/26; C08F 2220/1883; C08F 226/10; C08F 265/00; C08F 265/04; C08F 283/06

See application file for complete search history.

(56) References Cited

U.S. PATENT DOCUMENTS

| | | | |
|---|---|---|---|
| 4,847,410 A | 7/1989 | Lickei et al. | |
| 4,959,156 A | 9/1990 | Lickei et al. | |

(Continued)

FOREIGN PATENT DOCUMENTS

| | | |
|---|---|---|
| CA | 2570312 | 1/2006 |
| DE | 10338437 | 3/2005 |
| EP | 1681923 | 5/2005 |
| GB | 2 026 341 | 2/1980 |
| JP | 2006508159 | 3/2006 |
| WO | WO 03/043420 | 5/2003 |
| WO | WO 03039249 A2 * | 5/2003 |
| WO | WO 03/055944 | 7/2003 |
| WO | WO 03/086493 | 10/2003 |
| WO | 2004/100664 | 11/2004 |
| WO | WO 2004/100665 | 11/2004 |
| WO | WO 2005/046328 | 5/2005 |
| WO | WO 2005/121201 | 12/2005 |
| WO | WO 2006/000592 | 1/2006 |
| WO | WO 2006/051746 | 5/2006 |
| WO | WO 2008/064986 | 6/2008 |
| WO | WO 2008/064987 | 6/2008 |
| WO | WO 2008/064990 | 6/2008 |
| WO | WO 2008/065050 | 6/2008 |
| WO | WO 2008/132067 | 11/2008 |
| WO | WO 2008/132179 | 11/2008 |

OTHER PUBLICATIONS

International Preliminary Report on Patentability dated Dec. 4, 2008, from corresponding International Application No. PCT/EP200/060553, filed Oct. 4, 2007.
International Search Report completed Jan. 24, 2008, in International Application No. PCT/EP200/060553, filed Oct. 4, 2007.
English language translation of the International Preliminary Report on Patentability mailed May 14, 2009, from corresponding International Application No. PCT/EP2007/060553, filed Oct. 4, 2007.

*Primary Examiner* — Jean Cornet
(74) *Attorney, Agent, or Firm* — Brinks Gilson & Lione

(57) ABSTRACT

The present invention relates to novel comb polymers, to a process for their manufacture and to the use thereof in the stabilization in an aqueous phase of active or effect substances which are insoluble or sparingly soluble in water. The invention furthermore relates to the use of the comb polymers in the manufacture of active substance formulations or active substance preparations of water-insoluble active or effect substances, in particular of active substances for plant protection.
The comb polymers can be obtained by copolymerization of monoethylenically unsaturated monomers M, the monomers M comprising:
a) at least one monoethylenically unsaturated monomer Ma chosen from esters of monoethylenically unsaturated $C_3$-$C_8$-monocarboxylic acids with $C_1$-$C_{20}$-alkanols, $C_5$-$C_{10}$-cycloalkanols, phenyl-$C_1$-$C_4$-alkanols or phenoxy-$C_1$-$C_4$-alkanols and the diesters of monoethylenically unsaturated $C_4$-$C_8$-dicarboxylic acids (Continued)

with $C_1$-$C_{20}$-alkanols, $C_5$-$C_{10}$-cycloalkanols, phenyl-$C_1$-$C_4$-alkanols or phenoxy-$C_1$-$C_4$-alkanols; and b) at least one monoethylenically unsaturated monomer Mb chosen from the esters of monoethylenically unsaturated $C_3$-$C_8$-monocarboxylic acids and the mono- and diesters of monoethylenically unsaturated $C_4$-$C_8$-dicarboxylic acids with poly($C_2$-$C_4$-alkylene ether)ols;

and the total amount of the monomers Ma and Mb making up at least 60% by weight of the monomers M constituting the comb polymer.

22 Claims, No Drawings

(56) References Cited

U.S. PATENT DOCUMENTS

| | | |
|---|---|---|
| 5,468,821 A | 11/1995 | Lucast et al. |
| 6,074,986 A | 6/2000 | Mulqueen et al. |
| 6,248,805 B1 | 6/2001 | Nguyen et al. |
| 6,419,942 B1* | 7/2002 | Lo et al. ............... 424/408 |
| 2004/0197357 A1* | 10/2004 | Heming et al. ........... 424/401 |
| 2005/0090402 A1 | 4/2005 | Dieing et al. |
| 2005/0182219 A1 | 8/2005 | Meyer et al. |
| 2006/0116290 A1* | 6/2006 | Heming et al. ........... 504/360 |
| 2006/0229209 A1 | 10/2006 | Chrisstoffels et al. |
| 2007/0122436 A1 | 5/2007 | Koltzenburg et al. |
| 2008/0287593 A1 | 11/2008 | Oetter et al. |
| 2010/0029480 A1 | 2/2010 | Dieckmann et al. |
| 2010/0120617 A1 | 5/2010 | Dyllick-Brenzinger et al. |
| 2010/0122379 A1 | 5/2010 | Dieckmann et al. |

* cited by examiner

COMB POLYMERS AND USE THEREOF FOR THE PRODUCTION OF ACTIVE OR EFFECTIVE INGREDIENT FORMULATIONS

This application is a National Stage application of International Application No. PCT/EP2007/060553 filed Oct. 4, 2007, the entire contents of which is hereby incorporated herein by reference. This application also claims the benefit under 35 U.S.C. §119 of European Patent Application No. 06121851.7, filed Oct. 5, 2006, the entire contents of which is hereby incorporated herein by reference.

The present invention relates to novel comb polymers, to a process for their manufacture and to the use thereof in the stabilization in an aqueous phase of active or effect substances which are insoluble or sparingly soluble in water. The invention furthermore relates to the use of the comb polymers in the manufacture of active substance formulations or active substance preparations of water-insoluble active or effect substances, in particular of active substances for plant protection.

Active substances, i.e. substances which can already display a physiological action even in a low concentration, are frequently applied in the form of aqueous active substance preparations. Thus, for example in plant protection, the active substances used for combating pests, i.e. plant protection active substances, such as insecticides, acaricides, nematicides, fungicides and herbicides but also growth regulators, are frequently formulated and sold as concentrates, e.g. as aqueous concentrates, such as suspensions or emulsions, but also as solid concentrates, such as powders, dusts or granules. These formulations, before their application, are generally diluted to the desired use level by addition of a large amount of water ("spray mixture"). Also, for pharmaceutically and cosmetically active substances and for food additives, e.g. vitamins, provitamins, and the like, formulations which make it possible to stabilize or solubilize the active substance in an aqueous medium, for example in a liquid foodstuff or in an infusion solution but also in body fluids, have proven to be worthwhile. For effect substances too, i.e. low molecular weight compounds which already display a defined technical action at a low application rate, e.g. colorants and UV stabilizers, formulations are often necessary which make it possible to efficiently stabilize or solubilize the effective substance in an aqueous medium.

A main problem is represented by the generally low solubility in water of the active substances or effect substances, which is frequently less than 10 g/l at 23° C./1013 mbar. Aqueous formulations of such active substances and likewise aqueous ready-for-use preparations are accordingly heterogeneous systems in which the active substance is present as emulsified or dispersed phase in a continuous aqueous phase. Emulsifiers or dispersants are normally used to stabilize these per se metastable systems. However, the stabilizing action thereof is frequently unsatisfactory, so that the separation of the active substance, for example creaming or sedimentation of the active substance, can occur, in particular if the aqueous formulation is stored for a relatively long time at elevated temperature and/or at highly changeable temperatures or in the vicinity of the freezing point. This problem is then particularly pronounced if the active substance has a tendency to crystallize. Solid active substance particles also frequently separate if a formulation comprising the active substance in concentrated form is diluted with water.

Organic solvents are frequently used for the manufacture of formulations of water-insoluble active substances. Thus, water-miscible solvents are frequently used as solubilizing agents, i.e. for increasing the solubility of the active or effect substance in the aqueous phase. In turn, water-immiscible solvents are used to convert into a liquid phase an active substance which is solid at the temperature of use, in which the liquid phase can then be easily emulsified. In contrast to suspensions of the solid active substance, the active substance is dissolved at the molecular level in the solvent droplets in the emulsions and is accordingly, on application, more readily available and frequently more effective. However, the use of relatively large amounts of organic solvents is undesirable, on the basis of the well-known VOC problem, for reasons of health and safety at work, environmental aspects and partly also toxicological reasons.

An additional disadvantage of conventional aqueous active substance formulations is the comparatively large particle size of the active substance particles or active substance droplets suspended or emulsified in the aqueous phase, which is generally several µm. Aqueous formulations are desirable in which the active substance is present in the most finely divided form possible or, on diluting with water, is converted into a finely divided form, in order, on the one hand, to guarantee uniform distribution in the formulation and accordingly an improved ability to be handled and metered and simultaneously in order to increase the bioavailability of the active substance present in the formulation or in the ready-to-use composition. In this connection, formulations are desirable which, on diluting with water, result in an active substance preparation in which the phase comprising the active substance exhibits mean particle sizes of less than 500 nm and in particular less than 300 nm.

The use of amphiphilic block copolymers for the solubilization or stabilization of water-insoluble active substances in an aqueous vehicle has been proposed on several occasions (see, e.g., WO2005/121201 and the literature cited therein). The term "solubilization" describes a stable uniform distribution of the water-insoluble active or effect substance in the aqueous phase achieved by use of solubilizing substances (auxiliaries), the particles of the disperse active substance phase frequently being so small that they barely scatter visible light and the mixture accordingly appears more or less transparent. The amphiphilic block copolymers in this connection generally exhibit at least one hydrophilic polymer block and at least one hydrophobic polymer block. The manufacture of the block copolymers disclosed in WO 2005/121201 is comparatively expensive.

U.S. Pat. No. 4,847,410 and U.S. Pat. No. 4,959,156 disclose the manufacture of copolymers of allyl alcohol alkoxylates and (meth)acrylic acid and propose the use thereof as dispersants.

WO 03/043420 discloses the use of copolymers as adjuvants in the treatment of plants. The copolymers consist of olefins and/or vinyl ethers, and also of ethylenically unsaturated dicarboxylic acids or dicarboxylic acid derivatives and additional comonomers.

DE 10338437 discloses formulations of agrochemical active substances with adjuvants based on block copolymers which are provided by reaction of (a) modified polyolefins or oligoolefins with an end group derived from ethylenically unsaturated dicarboxylic acid with (b) polymers obtained by homo- or copolymerization of oxirane or aziridine derivatives.

WO 03/055944 discloses the use of copolymers based on acrylamidomethylpropane-sulfonic acid (AMPS) as crystallization inhibitor in aqueous suspension concentrates for plant protection.

EP 1 681 923 discloses active substance formulations comprising at least one active substance and at least one random copolymer which can be obtained by radical polymerization of olefinically unsaturated sulfonic acids with esters or amides of acrylic acid or methacrylic acid.

WO 06/000592 discloses the use of polymers comprising ether groups as solubilizing agents for the manufacture of plant protection compositions, it being possible for the polymers to be obtained by copolymerization of at least one hydrophobic monomer and at least one allyl alcohol alkoxylate.

However, the polymers disclosed in the state of the art are frequently, with regard to their solubilizing property, not satisfactory for active substances insoluble or sparingly soluble in water or it is expensive to manufacture them.

It is an object of the present invention to make available substances which make possible effective solubilization in an aqueous medium of active substances which are insoluble or sparingly soluble in water. These substances should be suitable for the manufacture of formulations which allow effective stabilization of the active substance in the aqueous phase. These substances should in particular also be suitable for making available active substance compositions of water-insoluble active substances which do not exhibit volatile organic substances or which exhibit only a very low content of volatile organic substances. Furthermore, a high stability of the active substance formulations manufactured using these substances is desirable with regard to separation processes on lengthy storage, on addition of electrolyte and on diluting with water. In addition, the substances should be easy to manufacture.

This object is achieved, surprisingly, by comb polymers which can be obtained by copolymerization of monoethylenically unsaturated monomers M, the monomers M comprising:

a) at least one monoethylenically unsaturated monomer Ma chosen from esters of monoethylenically unsaturated $C_3$-$C_8$-monocarboxylic acids with $C_1$-$C_{20}$-alkanols, $C_5$-$C_{10}$-cycloalkanols, phenyl-$C_1$-$C_4$-alkanols or phenoxy-$C_1$-$C_4$-alkanols and the diesters of monoethylenically unsaturated $C_4$-$C_8$-dicarboxylic acids with $C_1$-$C_{20}$-alkanols, $C_5$-$C_{10}$-cycloalkanols, phenyl-$C_1$-$C_4$-alkanols or phenoxy-$C_1$-$C_4$-alkanols; and b) at least one monoethylenically unsaturated monomer Mb chosen from the esters of monoethylenically unsaturated $C_3$-$C_8$-monocarboxylic acids and the mono- and diesters of monoethylenically unsaturated $C_4$-$C_8$-dicarboxylic acids with poly($C_2$-$C_4$-alkylene ether)ols;

and the total amount of the monomers Ma and Mb making up at least 60% by weight, in particular at least 70% by weight and especially at least 80% by weight of the monomers M constituting the comb polymer.

The invention accordingly relates to the comb polymers described here and to a process for their manufacture which comprises the radical copolymerization of the monomers M.

The comb polymers according to the invention are advantageously suitable for the stabilization in aqueous phase of active and effect substances which are sparingly soluble or insoluble in water and accordingly make possible the manufacture both of aqueous formulations of such active and effect substances and the manufacture of nonaqueous formulations which result, on diluting with water, in an extremely fine distribution of the active substance or effect substance in the aqueous phase. It is possible, by the comb polymers according to the invention and the use thereof, to solubilize in a stable fashion industrially relevant amounts of active or effect substance for the respective application without organic solvents being necessary for this.

Another subject matter of the present invention is accordingly the use of the comb polymers described here and subsequently for the stabilization, in an aqueous medium, of active substances and/or effect substances which are sparingly soluble or insoluble in water.

The subject matter of the present invention is furthermore the use of the comb polymers described here for the manufacture of formulations of active and effect substances which are insoluble or sparingly soluble in water.

The subject matter of the invention is furthermore active or effect substance formulations which comprise at least one active substance and/or effect substance which is sparingly soluble or insoluble in water and at least one comb polymer, as described here and subsequently.

An additional subject matter of the present invention is the use of comb polymers according to the invention in the manufacture of aqueous preparations of active substances and effect substances which exhibit a solubility in water at 25° C./1013 mbar of less than 10 g/l.

A further subject matter of the present invention is a process for the manufacture of aqueous active substance preparations, which comprises the mixing or diluting of an active substance formulation according to the invention with water.

The active or effect substance formulations according to the invention produce, on diluting with water or an aqueous liquid, aqueous preparations of the active or effect substance which comprise an aqueous continuous phase and at least one phase comprising active substance or effect substance with a mean particle size clearly of less than 1 μm, typically of not more than 500 nm, frequently of not more than 400 nm, in particular of not more than 300 nm, particularly preferably of not more than 250 nm, 200 nm or 150 nm and especially of not more than 100 nm, e.g. ranging from 5 to 500 nm or from 5 to 400 nm, frequently ranging from 10 to 300 nm, preferably ranging from 10 to 250 nm, in particular ranging from 20 to 200 nm or 20 to 150 nm and particularly preferably ranging from 20 to 100 nm. Depending on the type of polymer and the active substance or effect substance, and depending on the ratios of concentrations, the aggregates can even be so small that they are no longer present in the form of detectable discrete particles (particle size <20 nm, <10 nm or <5 nm).

The particle sizes given here and below are weight-average particle sizes, as can be determined by dynamic light scattering. Methods for this are familiar to a person skilled in the art, for example from H. Wiese in D. Distler, Wässrige Polymerdispersionen [Aqueous Polymer Dispersions], Wiley-VCH, 1999, Chapter 4.2.1, p. 40ff and the literature cited therein, and also H. Auweter and D. Horn, J. Colloid Interf. Sci., 105 (1985), 399, D. Lilge and D. Horn, Colloid Polym. Sci., 269 (1991), 704, or H. Wiese and D. Horn, J. Chem. Phys., 94 (1991), 6429.

Active substances in the sense of the present invention are chemically defined substances which, in an organism, selectively give rise to an action or a reaction, generally even when applied in small amounts. Effect substances are chemically defined substances which selectively bestow a property on inanimate matter, generally even when applied in small amounts. Since an action on organisms brought into contact with the inanimate material can result indirectly or directly from this property, the terms "active substance" and "effect substance" are frequently used synonymously, also in the context of this patent application. Active or effect substances in the sense of this invention are in particular organic compounds with a defined molecular composition (empirical formula) and a molecular weight which is typically not more than 2000 daltons, in particular not more than 1000 daltons, and preferably ranging from 100 to 1000 daltons and especially ranging from 150 to 500 daltons. In this connection, sparingly soluble means a solubility of the active or effect substance in water of less than 10 g/l, frequently of less than 5 g/l and in particular of less than 1 g/l and especially of less than 0.1 g/l, at 25° C. and 1013 mbar.

The active or effect substance formulations according to the invention can be solid, pasty or liquid.

The terms "aqueous medium" and "aqueous phase" comprise, here and subsequently, water, aqueous mixtures of water with up to 10% by weight, based on the mixture, of organic solvents which are miscible with water, and solutions of solids in water or in aqueous mixtures. Examples of water-miscible solvents comprise $C_3$-$C_4$-ketones, such as acetone and methyl ethyl ketone, cyclic ethers, such as dioxane and tetrahydrofuran, $C_1$-$C_4$-alkanols, such as methanol, ethanol, n-propanol, isopropanol, n-butanol or tert-butanol, polyols and the mono- and dimethyl ethers thereof, such as glycol, propanediol, ethylene glycol monomethyl ether, diethylene glycol, diethylene glycol monomethyl ether, diethylene glycol dimethyl ether or glycerol, furthermore $C_2$-$C_3$-nitriles, such as acetonitrile and propionitrile, dimethyl sulfoxide, dimethylformamide, formamide, acetamide, dimethylacetamide, butyrolactone, 2-pyrrolidone and N-methylpyrrolidone.

The term "active substance formulation" is used, here and subsequently, synonymously with the term "formulation", i.e. in the sense of a composition which comprises the active substance in concentrated form and which, for application, is, if appropriate, diluted with water or aqueous liquids to the desired use concentration.

The formulations according to the invention, but also the active substance preparations obtained by diluting a formulation according to the invention with water, are distinguished by an extremely high stability with regard to phase separations. They can be stored without phase separation over a relatively lengthy period of time of several months, even at elevated temperature and/or with strongly varying temperatures. Furthermore, concentrated formulations can also be diluted with water without problems, without phase separation phenomena, such as coagulation, crystallization, flocculation or sedimentation, arising. In addition, the compositions according to the invention (i.e. aqueous formulations and aqueous active or effect substance preparations) exhibit a high tolerance with regard to electrolytes. Moreover, because of the extremely fine distribution, corresponding to the very low apparent particle diameter of the active substance and/or effect substance aggregates, the activity of the active substances or the action of the effect substances is increased in comparison with conventional formulations. An additional advantage is that the active substance formulations according to the invention can also be formulated with little solvent (content of volatile solvents <10% by weight, based on the weight of the active substance formulation) or even with no solvent (content of volatile solvents <1% by weight, based on the weight of the active substance formulation).

An additional advantage of the comb polymers according to the invention is to be seen in that, with their help, active substances in solid form can be formulated and these solid or pasty formulations can be diluted with water, the active substances being obtained in the abovementioned particle sizes.

In the context of the present invention, the expression "$C_1$-$C_{20}$-alkyl" is used for a linear or branched alkyl group exhibiting 1 to 20 carbon atoms, e.g. for $C_1$-$C_4$-alkyl and for pentyl, hexyl, 1-methylpentyl, 2-methylpentyl, heptyl, octyl, 1-methylheptyl, 2-methylheptyl, 2,4,4-trimethylpentan-2-yl, 2-ethylhexyl, 1-ethylhexyl, nonyl, isononyl, decyl, 1-methylnonyl, 2-propylheptyl and the like. $C_1$-$C_4$-Alkyl is a linear or branched alkyl group exhibiting 1 to 4 carbon atoms, e.g. methyl, ethyl, n-propyl, isopropyl, n-butyl, 2-butyl, 2-methylpropan-1-yl or tert-butyl.

The expression "cycloalkyl" comprises, in the sense of the present invention, both unsubstituted and substituted cycloalkyl groups, preferably $C_5$-$C_7$-cycloalkyl groups, such as cyclopentyl, cyclohexyl or cycloheptyl. These can, in the case of a substitution, generally carry 1, 2, 3, 4 or 5 substituents, preferably 1, 2 or 3 substituents and particularly preferably 1 substituent. Preferably, these substituents are chosen from alkyl, alkoxy and halogen.

The expression "phenylalkyl" comprises, in the sense of the present invention, linear or branched alkyl groups, in particular linear alkyl groups, which are substituted by an optionally substituted phenyl group, this phenyl group carrying, in the case of a substitution, generally 1, 2, 3, 4 or 5 substituents, preferably 1, 2 or 3 substituents and particularly preferably one substituent, preferably chosen from alkyl, alkoxy, trifluoromethyl, di($C_1$-$C_4$-alkyl)amino, nitro, cyano or halogen. In particular, the phenyl group in phenylalkyl is unsubstituted.

The expression "phenoxyalkyl" comprises, in the sense of the present invention, linear or branched alkyl groups, in particular linear alkyl groups, which are substituted by an optionally substituted phenoxy group via the oxygen atom of the phenoxy group, this phenoxy group carrying, in the case of a substitution, generally 1, 2, 3, 4 or 5 substituents, preferably 1 or 2 substituents, preferably chosen from alkyl, alkoxy, carboxyl, trifluoromethyl, sulfonate ($SO_3$—), amino, $C_1$-$C_4$-alkylamino, di($C_1$-$C_4$-alkyl)amino, nitro, cyano or halogen. In particular, the phenoxy group in phenoxyalkyl is unsubstituted.

The preferred meanings (or meanings given as frequently or in particular), particularly preferred meanings and specific meanings given here and below with regard to the comb polymers, in particular type and constituent amounts of monomers in the comb polymers, the molecular weight thereof, and also with regard to the formulations and active or effect substance preparations, in particular with regard to the type of the formulation, the type of the active or effect substances, the concentration thereof in the formulations according to the invention, particle sizes, mass ratios of comb polymer to active or effect substance, type and amount of additives, and the like, are to be understood fundamentally independently of one another, preferably though in any combination (i.e. in combination of two or more or all of these meanings). That is, combinations of two or more or all of these meanings represent preferred, particularly preferred and specific embodiments of the invention.

The esters of monoethylenically unsaturated monocarboxylic acids with 3 to 8 carbon atoms include, for example, the esters of acrylic acid, methacrylic acid, crotonic acid and isocrotonic acid. The diesters of monoethylenically unsaturated dicarboxylic acids with 4 to 8 carbon atoms include, for example, the diesters of maleic acid, fumaric acid and itaconic acid.

Preference is given to esters of monoethylenically unsaturated $C_3$-$C_8$-monocarboxylic acids and, among these, in particular to the esters of acrylic acid and methacrylic acid.

The diesters of monoethylenically unsaturated $C_4$-$C_8$-dicarboxylic acids include in particular the esters of fumaric acid, itaconic acid and maleic acid.

Preference is given to the monomers Ma chosen from esters of acrylic acid with $C_1$-$C_{20}$-alkanols, in particular $C_1$-$C_{10}$-alkanols, such as methyl acrylate, ethyl acrylate, n-butyl acrylate, 2-butyl acrylate, isobutyl acrylate, tert-butyl acrylate, 2-ethylhexyl acrylate, decyl acrylate, lauryl acrylate and stearyl acrylate, esters of acrylic acid with $C_5$-$C_{10}$-cycloalkanols, such as cyclohexyl acrylate, esters of acrylic acid with phenyl-$C_1$-$C_4$-alkanols, such as benzyl acrylate, 2-phenylethyl acrylate and 1-phenylethyl acrylate, esters of acrylic acid with phenoxy-$C_1$-$C_4$-alkanols, such as 2-phenoxyethyl acrylate, the esters of methacrylic acid with $C_1$-$C_{20}$-alkanols, preferably $C_1$-$C_{10}$-alkanols, such as methyl methacrylate, ethyl methacrylate, n-butyl methacrylate, 2-butyl methacrylate, isobutyl methacrylate, tert-butyl methacrylate, 2-ethylhexyl methacrylate, decyl methacrylate, lauryl methacrylate and stearyl methacrylate, esters of methacrylic acid with $C_5$-$C_{10}$-cycloalkanols, such as cyclohexyl methacrylate, esters of methacrylic acid with phenyl-$C_1$-$C_4$-alkanols, such as benzyl methacrylate, 2-phenylethyl methacrylate and 1-phenylethyl methacrylate, and esters of methacrylic acid with phenoxy-$C_1$-$C_4$-alkanols, such as 2-phenoxyethyl methacrylate.

In a particularly preferred embodiment, the monomers Ma comprise to at least 80%, based on the total amount of the monomers Ma, and in particular exclusively, esters of acrylic acid and/or methacrylic acid with $C_1$-$C_{12}$-alkanols. In a very particularly preferred embodiment, the monomers Ma comprise to at least 80%, based on the total amount of the monomers Ma, and in particular exclusively, esters of acrylic acid and/or methacrylic acid with $C_1$-$C_6$-alkanols, especially methyl acrylate, methyl methacrylate and/or butyl acrylate. In a likewise very particularly preferred embodiment, the monomers Ma comprise to at least 80%, based on the total amount of the monomers Ma, and in particular exclusively, a mixture of at least one monomer Ma(1), which is chosen from esters of acrylic acid and methacrylic acid with $C_1$-$C_5$-alkanols, especially methyl acrylate, methyl methacrylate and/or butyl acrylate, with at least one monomer Ma(2), which is chosen from esters of acrylic acid and methacrylic acid with $C_6$-$C_{20}$-alkanols, especially lauryl acrylate, stearyl acrylate, lauryl methacrylate and/or stearyl methacrylate, and esters of acrylic acid and methacrylic acid with phenoxy-$C_1$-$C_4$-alkanols, such as 2-phenoxyethyl acrylate and 2-phenoxyethyl methacrylate.

Preferably, the proportion of monomers Ma, based on the total monomer amount of the monomers M, is from 10 to 90% by weight, preferably from 20 to 88% by weight and especially from 40 to 85% by weight.

The monoethylenically unsaturated monomers Mb are chosen from esters comprising polyether groups, these being formed from a monoethylenically unsaturated $C_3$-$C_8$-monocarboxylic acid or $C_4$-$C_8$-dicarboxylic acid and one, respectively two, poly($C_2$-$C_4$-alkylene ether)ols.

The poly(alkylene ether)ols on which the monomers Mb are based are linear or branched, in particular linear. Depending on the degree of branching and the end groups, the poly($C_2$-$C_4$-alkylene ether)ols on which the esters are based can be both monools and polyols, e.g. diols or triols. Monools and diols are preferred, in particular monools.

It has proven to be advantageous for at least 50 mol %, in particular at least 80 mol %, particularly preferably 90 mol % and in particular all of the repeat units forming the poly($C_2$-$C_4$-alkylene ether)ols to be $CH_2$—$CH_2$—O. That is, in the poly($C_2$-$C_4$-alkylene ether)ols, the proportion of copolymerized ethylene oxide is at least 50 mol %, in particular at least 80 mol %, particularly preferably 90 mol % and in particular 100 mol %, based on the total amount of all repeat units in the poly($C_2$-$C_4$-alkylene ether)ol. These % figures are the number-average values, based on the total amount of polyether groups in the comb polymer.

Preference is given to the poly($C_2$-$C_4$-alkylene ether)ols on which the monomers Mb are based chosen from poly-$C_2$-$C_4$-alkylene glycol mono-$C_1$-$C_{10}$-alkyl ethers.

In particular, the poly($C_2$-$C_4$-alkylene ether)ols on which the monomers Mb are based exhibit a number-average molecular weight in the range from 200 to 10 000, especially in the range from 800 to 2000.

Preference is given to the poly($C_2$-$C_4$-alkylene ether)ols on which the monomers Mb are based chosen from alcohols of the general formula (I)

$$\text{HO-(Alk-O)}_n\text{—Z} \qquad (I)$$

in which

Z is hydrogen, $C_1$-$C_{20}$-alkyl or benzyl, in particular $C_1$-$C_{10}$-alkyl, especially methyl or ethyl, n is an integer, the number-average value of which ranges from 5 to 300, preferably from 5 to 200, in particular from 10 to 100 and especially from 15 to 50, Alk is $C_2$-$C_4$-alkylene, in particular 1,2-ethanediyl and/or 1,2-propanediyl, it being possible for Alk in each repeat unit (Alk-O)$_n$ each time to be identical or different.

Preference is in particular given to monoethylenically unsaturated monomers Mb chosen from esters of the general formula (II)

$$\text{A-B—CH}=\text{C(R}^1\text{)—C(=O)—O-(Alk-O)}_n\text{—Z} \qquad (II),$$

in which

Z is hydrogen, $C_1$-$C_{20}$-alkyl or benzyl, in particular $C_1$-$C_{10}$-alkyl, B is a chemical bond or $CH_2$, in particular a chemical bond, n is an integer, the mean value of which, based on the comb polymer, ranges from 5 to 300, preferably from 5 to 200, in particular from 10 to 100 and especially from 15 to 50, Alk is $C_2$-$C_4$-alkylene, in particular 1,2-ethanediyl and/or 1,2-propanediyl, it being possible for Alk in each different repeat unit (Alk-O)$_n$ in each case to be identical or different, $R^1$ is hydrogen or methyl, in particular methyl, and A is hydrogen, C(O)OH or C(O)O(Alk'-O)$_m$Z', in which Alk' has one of the meanings given previously for Alk, Z' has one of the meanings given previously for Z and m has one of the meanings given previously for n, A being in particular hydrogen.

In view of the use according to the invention, it has proven to be advantageous for the mean number of repeat units Alk-O in the groups (Alk-O)$_n$ or (Alk'-O)$_m$, i.e. the number average of n or m in the formulae (I) and (II), to be at least 5, in particular at least 10 and especially at least 15 and for a value of 200, in particular 100 and especially 50 not to be exceeded. Preferably, the value ranges from 5 to 200, in particular ranges from 10 to 100 and especially ranges from 15 to 50. The mean value of n or m is the number-average value, based on all polyether groups in the comb polymer.

The alkylene parts of the individual repeat units Alk-O or Alk'-O in the groups (Alk-O)$_n$ or (Alk'-O)$_m$ can be identical or different. Particularly preferably, Alk-O or Alk'-O is 1,2-ethanediyl or mixtures of 1,2-ethanediyl with 1,2-propanediyl. If the groups (Alk-O)$_n$ or (Alk'-O)$_m$ exhibit units Alk-O or Alk'-O differing from one another, these can be arranged randomly or blockwise, a blockwise arrangement being preferred.

If the groups (Alk-O)$_n$ or (Alk'-O)$_m$ exhibit different repeat units Alk-O or Alk'-O, it has proven to be advantageous for, on average, at least 50 mol %, e.g. 50 to 99 mol %, in particular at least 80 mol %, e.g. 80 to 99 mol %, and especially at least 90 mol %, e.g. 90 to 98 mol %, of the groups Alk-O or Alk'-O to be CH$_2$—CH$_2$—O. Among these, those mixtures are preferred in which the remaining repeat units Alk-O or Alk'-O are CH(CH$_3$)—CH$_2$—O.

In particular, the monomers Mb are chosen from esters of monoethylenically unsaturated C$_3$-C$_8$-monocarboxylic acids with poly(C$_2$-C$_4$-alkylene ether)ols. In particular, the monomers Mb are chosen from esters of acrylic acid and methacrylic acid with poly(C$_2$-C$_4$-alkylene ether)ols. In particular, the monomers Mb are chosen from the esters of acrylic acid and methacrylic acid with the poly(C$_2$-C$_4$-alkylene ether)ols given previously as preferred and especially with the poly(C$_2$-C$_4$-alkylene ether)monools given as preferred. The monomers Mb chosen from the esters of acrylic acid and methacrylic acid with the poly-C$_2$-C$_4$-alkylene glycol mono-C$_1$-C$_{10}$-alkyl ethers given previously as preferred are very particularly preferred. In these preferred and very particularly preferred esters of acrylic acid and methacrylic acid, what has been said previously for the molecular weight of the polyetherols and the type and number of the repeat units is, of course, valid.

The proportion of the monomers Mb, based on the total monomer amount of the monomers M, typically ranges from 10 to 90% by weight, preferably from 12 to 80% by weight and especially from 15 to 60% by weight.

In addition to the monomers Ma and Mb, the monomers M constituting the comb polymer can also comprise additional monomers Mc different from the monomers Ma and Mb. The proportion of the monomers Mc to the total amount of the monomers M preferably makes up not more than 40% by weight, frequently not more than 30% by weight and in particular not more than 20% by weight.

In a preferred embodiment, the monomers comprise from 5% by weight up to 40% by weight, in particular from 5% by weight up to 30% by weight and especially from 5% by weight up to 20% by weight of the monomers Mc different from the monomers Ma and Mb.

The monomers Mc are preferably monoethylenically unsaturated, i.e. they exhibit only one polymerizable ethylenically unsaturated double bond.

The monomers Mc comprise both ionic or ionizable (i.e., acidic or basic) monomers Mc$^a$ and neutral monomers Mc$^b$. Ionic means that the monomers Mc$^a$ exhibit a functional group which exists in the charged state. Examples of ionic groups are anionic groups, such as carboxylate, sulfonate, phosphonate and phosphate, and cationic groups, in particular quaternary ammonium groups and protonated amino groups, including quaternary and protonated imidazolium groups and pyridinium groups. Ionizable means that the monomers Mc$^a$ exhibit a functional group which can be converted by protonation (in the case of a basic ionizable group) or by deprotonation (in the case of an acidic ionizable group) to an ionic group, as mentioned previously.

Preferred monomers Mc$^a$ are chosen from anionic and acidic monomers Mc$^a$, in particular from those exhibiting at least one carboxylic acid group or one sulfonic acid group.

The preferred monomers Mc$^a$ include in particular monoethylenically unsaturated monomers with at least one carboxylic acid group, in particular monoethylenically unsaturated mono- and dicarboxylic acids with 3 to 8 carbon atoms, such as acrylic acid, methacrylic acid, vinylacetic acid, crotonic acid, fumaric acid, maleic acid, itaconic acid and the like, and also the anhydrides of the abovementioned monoethylenically unsaturated dicarboxylic acids, the proportion of the monomers Mc generally not exceeding 20% by weight and in particular 10% by weight, based on the total amount of monomers M.

The monomers Mc$^a$ furthermore include monoethylenically unsaturated monomers exhibiting at least one sulfonic acid group. Examples of such monomers Mc$^a$ are styrenesulfonic acid, vinylsulfonic acid, allylsulfonic acid, methallylsulfonic acid and the monomers defined by the following general formula III.

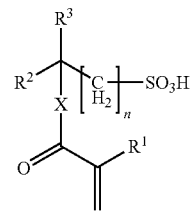

In formula III:

n is 0, 1, 2 or 3, in particular 1 or 2;

x is O or NR$^5$;

R$^1$ is hydrogen or methyl;

R$^2$ and R$^3$ are, independently of one another, hydrogen or C$_1$-C$_4$-alkyl, in particular hydrogen or methyl; and R$^5$ is hydrogen or C$_1$-C$_4$-alkyl, in particular hydrogen.

Examples of monomers Mc$^a$ of the general formula I are 2-acrylamido-2-methylpropanesulfonic acid, 2-methacrylamido-2-methylpropanesulfonic acid, 2-acrylamidoethanesulfonic acid, 2-methacrylamidoethanesulfonic acid, 2-acryloyloxyethanesulfonic acid, 2-methacryloyloxyethanesulfonic acid, 3-acryloyloxypropanesulfonic acid and 2-methacryloyloxypropanesulfonic acid. In preferred embodiments, the comb polymers do not comprise, copolymerized, any monomer having sulfonic acid groups.

The monomers Mc$^b$ include neutral monoethylenically unsaturated monomers which, unlike the monomers Mc$^a$, exhibit no ionic or ionizable group. Preference is in particular given among these to those monomers Mc$^b$ which exhibit an increased solubility in water, in particular a solubility of at least 60 g/l at 25° C. and 1013 mbar. Such monomers with increased solubility in water or even miscibility in water are known to a person skilled in the art, e.g. from Ullmann's Encyclopedia of Industrial Chemistry, "Polyacrylates", 5th ed. on CD-ROM, Wiley-VCH, Weinheim, 1997. Typical monomers Mc$^b$ are hydroxy-C$_2$-C$_4$-alkyl esters of monoethylenically unsaturated monocarboxylic acids, in particular of acrylic acid and methacrylic acid, such as 2-hydroxyethyl acrylate, 2-hydroxypropyl acrylate, 3-hydroxypropyl acrylate, 2-hydroxybutyl acrylate, 4-hydroxybutyl acrylate, 2-hydroxyethyl methacrylate, 2-hydroxypropyl methacrylate, 3-hydroxypropyl methacrylate, 2-hydroxybutyl methacrylate or 4-hydroxybutyl methacrylate, furthermore amides of monoethylenically unsaturated monocarboxylic acids, such as acrylamide or methacrylamide, furthermore acrylonitrile and methacrylonitrile, N-vinyllactams, such as N-vinylpyrrolidone or N-vinylcaprolactam, N-vinylamides of aliphatic C$_1$-C$_4$-monocarboxylic acids, such as N-vinylformamide or N-vinylacetamide, monoethylenically unsaturated monomers carrying urea groups, such as N-vinyl- and N-allylurea, and also imidazolidin-2-one derivatives, e.g. N-vinyl- and N-allylimidazolidin-2-one, N-vinyloxyethyl-imidazolidin-2-one, N-allyloxyethyl-imidazolidin-2-one, N-(2-acrylamidoethyl)imidazolidin-2-one, N-(2-acryloyloxy-ethyl)imidazolidin-2-one, N-(2-methacrylamidoethyl)

imidazolidin-2-one, N-(2-methacryloyloxyethyl)imidazolidin-2-one (=ureido methacrylate), N-[2-(acryloyloxyacetamido)ethyl]imidazolidin-2-one, N-[2-(2-acryloyloxyacetamido)-ethyl]imidazolidin-2-one, N-[2-(2-methacryloyloxyacetamido)ethyl]imidazolidin-2-one; and the like. The monomers $Mc^b$ are preferably chosen from hydroxy-$C_1$-$C_4$-alkyl esters of acrylic acid and methacrylic acid, acrylamide, methacrylamide, acrylonitrile or N-vinyllactams, the hydroxy-$C_2$-$C_4$-alkyl esters of acrylic acid and methacrylic acid being particularly preferred. In a very particularly preferred embodiment, the monomers $Mc^b$ comprise to at least 80% by weight, based on the total amount of the monomers Mc, at least one hydroxy-$C_2$-$C_4$-alkyl ester of acrylic acid and/or methacrylic acid and/or N-vinylcaprolactam.

In a preferred embodiment, the monomers Mc are chosen from the monomers $Mc^a$, in particular from monomers $Mc^a$ with a solubility in water of greater than 60 g/l at 20° C. and especially from monoethylenically unsaturated monomers with at least one carboxylic acid group. In a specific embodiment, the monomers Mc are chosen from monoethylenically unsaturated $C_3$-$C_8$-monocarboxylic acids and monoethylenically unsaturated $C_4$-$C_8$-dicarboxylic acids and in particular from monoethylenically unsaturated $C_3$-$C_6$-monocarboxylic acids and monoethylenically unsaturated $C_4$-$C_6$-dicarboxylic acids.

In a likewise preferred embodiment, the monomers Mc are chosen from the monomers $Mc^b$, in particular from monomers $Mc^b$ with a solubility in water of greater than 60 g/l at 20° C. and especially from amides of acrylic acid and methacrylic acid, the hydroxy-$C_1$-$C_4$-alkyl esters of acrylic acid and methacrylic acid, and N-vinyllactams, hydroxy-$C_2$-$C_4$-alkyl esters of acrylic acid and/or methacrylic acid and N-vinylcaprolactam being particularly preferred.

Preference is furthermore given according to the invention to comb polymers which exhibit a number-average molecular weight $M_n$ ranging from 2000 to 500 000 daltons, frequently ranging from 5000 to 100 000 daltons and in particular from 10 000 to 50 000 daltons. The weight-average molecular weight generally ranges from 2000 to 1 000 000 daltons, frequently ranges from 3000 to 200 000 daltons, in particular ranges from 4000 to 100 000 daltons and especially ranges from 10 000 to 50 000 daltons.

The ratio $M_w/M_n$ frequently ranges from 1.1:1 to 10:1, in particular ranges from 1.2:1 to 5:1. The molar masses $M_w$ and $M_n$ and the heterogeneity of the comb polymers are determined by size exclusion chromatography (=gel permeation chromatography or just GPC). Commercial poly(methyl methacrylate) (PMMA) standard units can be used as calibration material.

Generally, the comb polymer according to the invention will exhibit a glass transition temperature $T_g$ ranging from −80° C. to 160° C. and frequently ranging from −40° C. to +100° C. The term "glass transition temperature $T_g$" is understood here to mean the "midpoint temperature" determined according to ASTM D 3418-82 by differential scanning calorimetry (DSC) (cf. Ullmann's Encyclopedia of Industrial Chemistry, 5th Edition, Volume A 21, VCH Weinheim, 1992, p. 169, and also Zosel, Farbe und Lack, 82 (1976), pp. 125-134, see also DIN 53765).

In this connection, it proves to be helpful to estimate the glass transition temperature $T_g$ of the comb polymer with the help of the Fox equation (T. G. Fox, Bull. Am. Phys. Soc. (Ser. II), 1, 123 [1956], and Ullmann's Encyclopedia of Industrial Chemistry, Weinheim (1980), pp. 17-18) from the glass transition temperatures of the respective homopolymers of the monomers M constituting the polymer. The latter are known, e.g., from Ullmann's Encyclopedia of Industrial Chemistry, VCH, Weinheim, Vol. A 21 (1992), p. 169, or from J. Brandrup and E. H. Immergut, Polymer Handbook, 3rd ed., J. Wiley, New York, 1989.

An additional subject matter of the present invention relates to a process for the manufacture of the comb polymers according to the invention, which comprises the radical polymerization of the monomers M.

The comb polymers present in the formulations according to the invention can be manufactured according to conventional methods by radical polymerization of the monomers M. The polymerization can be carried out by free radical polymerization or by controlled radical polymerization processes. The polymerization can be carried out using one or more initiators and as solution polymerization, as emulsion polymerization, as suspension polymerization, as precipitation polymerization or as bulk polymerization. The polymerization can be carried out batchwise, semicontinuously or continuously.

The reaction times generally range between 1 and 12 hours. The temperature range in which the reactions can be carried out generally extends from 20 to 200° C., preferably from 40 to 120° C. The polymerization pressure is of secondary importance and can be carried out in the range from standard pressure or slight negative pressure, e.g. >800 mbar, or under positive pressure, e.g. up to 10 bar, it being possible for higher or lower pressures likewise to be used.

Conventional radical-forming substances are used as initiators for the radical polymerization. Preference is given to initiators chosen from the groups of the azo compounds, of the peroxide compounds and of the hydroperoxide compounds. The peroxide compounds include, for example, acetyl peroxide, benzoyl peroxide, lauroyl peroxide, tert-butylperoxy isobutyrate or caproyl peroxide. In addition to hydrogen peroxide, the hydroperoxides also include organic peroxides, such as cumene hydroperoxide, tert-butyl hydroperoxide, tert-amyl hydroperoxide and the like. The azo compounds include, for example, 2,2'-azobisisobutyronitrile, 2,2'-azobis(2-methylbutyronitrile), 2,2'-azobis[2-methyl-N-(2-hydroxyethyl)propionamide], 1,1'-azobis(1-cyclohexanecarbonitrile), 2,2'-azobis(2,4-dimethylvaleronitrile) or 2,2'-azobis(N,N'-dimethyleneisobutyroamidine). Azobisisobutyronitrile (AIBN) is particularly preferred. The initiator is normally used in an amount of from 0.02 to 5% by weight and in particular from 0.05 to 3% by weight, based on the amount of the monomers M, it also being possible to use larger amounts, e.g. up to 30% by weight, for example in the case of hydrogen peroxide. The optimum amount of initiator naturally depends on the initiator system used and can be determined by a person skilled in the art in routine experiments.

The initiator can be partially or completely introduced into the reaction vessel. Preferably, the bulk of the initiator, in particular at least 80%, e.g. from 80 to 100%, of the initiator, is added to the polymerization reactor in the course of the polymerization.

The molecular weight of the comb polymers can self-evidently be adjusted by addition of a small amount of regulators, e.g. from 0.01 to 5% by weight, based on the polymerizing monomers M. Suitable regulators are in particular organic thio compounds, e.g. mercaptoalcohols, such as mercaptoethanol, mercaptocarboxylic acids, such as thioglycolic acid or mercaptopropionic acid, or alkyl mercaptans, such as dodecyl mercaptan, and furthermore allyl alcohols and aldehydes.

The comb polymers are manufactured in particular by radical solution polymerization in an organic solvent or solvent mixture. Examples of organic solvents are alcohols, such as, e.g., methanol, ethanol, n-propanol and isopropanol, dipolar aprotic solvents, e.g. N-alkyllactams, such as N-methylpyrrolidone (NMP) or N-ethylpyrrolidone, furthermore dimethyl sulfoxide (DMSO) or N,N-dialkylamides of aliphatic carboxylic acids, such as N,N-dimethylformamide (DMF) or N,N-dimethylacetamide, or furthermore aromatic, aliphatic and cycloaliphatic hydrocarbons which may be halogenated, such as hexane, chlorobenzene, toluene or benzene, and mixtures thereof. Preferred solvents are isopropanol, methanol, toluene, DMF, NMP, DMSO and hexane. DMF is particularly preferred. Furthermore, the comb polymers can be prepared in a mixture with water of the solvents and solvent mixtures described previously. The proportion of water in these mixtures is, in this connection, preferably less than 50% by volume and in particular less than 10% by volume.

An additional subject matter of the present invention relates to formulations, which comprise:
i) at least one of the comb polymers described previously and
ii) at least one organic active substance and/or effect substance which exhibits a solubility in water at 25° C./1013 mbar of less than 10 g/l.

In the active substance formulations according to the invention, it has proved to be advantageous for the ratio by weight of active substance and/or effect substance to comb polymer to range from 1:10 to 3:1 and in particular from 1:5 to 2:1. Accordingly, the comb polymer is present in the active substance formulations according to the invention typically in an amount of 0.3 to 10 parts by weight, in particular of 0.5 to 8 parts by weight and especially of 1 to 5 parts by weight, based on 1 part by weight of active substance or effect substance.

A preferred embodiment of the invention relates to a solid or pasty active substance formulation which comprises at least one active substance and/or effect substance exhibiting a solubility in water at 25° C./1013 mbar of less than 10 g/l and at least one comb polymer according to the invention. The formulation essentially comprises no or only small amounts, i.e. <10% by weight, of water or organic solvents. These compositions can comprise, as additional constituents, the auxiliaries and additives typical for the respective applicational purpose. The proportion of the auxiliaries and additives will typically not exceed 30% by weight, in particular 20% by weight and especially 10% by weight, based on the total weight of the solid or pasty active substance formulation. Pasty means in this connection that the mixture is highly viscous, i.e. thick, and exhibits at least a honey-like consistency, the viscosity typically being at least 50 Pa·s, in particular at least 100 Pa·s (according to DIN 53019-2 at 25° C.).

The proportion of comb polymer in the solid or pasty active substance formulation is typically at least 20% by weight and frequently ranges from 20 to 95% by weight, in particular ranges from 30 to 90% by weight and especially ranges from 40 to 85% by weight, based on the total weight of the formulation. The proportion of active or effect substance frequently ranges from 5 to 70% by weight, in particular ranges from 10 to 60% by weight and especially ranges from 15 to 50% by weight. The proportion of other constituents, such as water, organic solvents, auxiliaries and additives, will typically not exceed 30% by weight, in particular 20% by weight and especially 10% by weight, based on the total weight of the solid or pasty active substance formulation.

An additional embodiment of the formulations according to the invention relates to a liquid formulation. These liquid formulations comprise at least one active or effect substance which is sparingly soluble or insoluble in water, at least one comb polymer according to the invention and a liquid solvent or diluent.

In addition to water, suitable solvents or diluents are also organic solvents, in particular those which are miscible with water, and also mixtures of these solvents with water. Examples of water-miscible solvents comprise $C_3$-$C_4$-ketones, such as acetone and methyl ethyl ketone, cyclic ethers, such as dioxane and tetrahydrofuran, $C_1$-$C_4$-alkanols, such as methanol, ethanol, n-propanol, isopropanol, n-butanol or tert-butanol, polyols and the mono- and dimethyl ethers thereof, such as glycol, propanediol, ethylene glycol monomethyl ether, diethylene glycol, diethylene glycol monomethyl ether, diethylene glycol dimethyl ether or glycerol, cyclic carbonates with 3 to 6 carbon atoms, such as ethylene carbonate (=1,3-dioxolan-2-one), as well as, furthermore, $C_2$-$C_3$-nitriles, such as acetonitrile and propionitrile, dimethyl sulfoxide, dimethylformamide, formamide, acetamide, dimethylacetamide, butyrolactone, 2-pyrrolidone and N-methylpyrrolidone.

Water or an aqueous medium which comprises up to 10% by weight, based on the weight of the aqueous medium, of one or more organic water-miscible solvents is preferred diluent. Formulations which comprise water or an aqueous medium as diluent comprise water or an aqueous medium as continuous phase and at least one disperse phase composed essentially of the at least one active substance and/or effect substance and the at least one comb polymer according to the invention. The active or effect substance and the comb polymer are presumably present in these aqueous active substance formulations in the form of aggregates of active substance or effect substance and the comb polymers according to the invention. This phase comprising active or effect substance accordingly forms a disperse phase which comprises the active substance or the effect substance and the at least one comb polymer according to the invention.

The active substance is present in the continuous aqueous phase in an extremely finely divided form. It is assumed that the active substance forms, in the aqueous phase, aggregates with the comb polymer according to the invention. These aggregates generally exhibit mean particle sizes of less than 1 μm, frequently of less than 500 nm, in particular of less than 400 nm, especially of less than 300 nm and very especially of less than 200 nm.

The proportion of comb polymer in the liquid active substance formulation is typically at least 5% by weight and frequently ranges from 5 to 50% by weight, in particular ranges from 7 to 40% by weight and especially ranges from 10 to 35% by weight, based on the total weight of the formulation. The proportion of active or effect substance frequently ranges from 0.5 to 40% by weight, in particular ranges from 1 to 30% by weight and in particular ranges from 5 to 25% by weight. The proportion of diluent typically ranges from 10 to 94.5% by weight, in particular ranges from 25 to 92% by weight and especially ranges from 30 to 85% by weight. The proportion of other auxiliaries and additives will typically not exceed 10% by weight, in particular 5% by weight, based on the total weight of the liquid active substance formulation.

The active substance formulation according to the invention can be manufactured in different ways. Typically, the manufacture of the active substance or effect substance formulation according to the invention comprises the manufacture or preparation of a homogeneous nonaqueous mixture which comprises the comb polymers according to the invention and at least one active substance and/or effect substance.

According to a first preferred embodiment of the present invention, the process comprises the preparation of a homogeneous nonaqueous mixture comprising at least one comb polymer according to the invention and at least one active substance and/or effect substance. This mixture is, if it comprises no liquid constituents, generally solid or highly viscous or pasty and is described, here and subsequently, as solid or pasty formulation.

For the preparation of the homogeneous nonaqueous mixture, the active substance will generally be incorporated in a liquid form of the comb polymer, for example in a melt of the comb polymer or, preferably, in a solution of the comb polymer in an organic solvent. The incorporation can also be carried out by extrusion of a mixture of active substance and comb polymer and, if appropriate, solvent. If a solvent is used, the solvent will subsequently be removed to the greatest possible extent and preferably completely, e.g. by distillation (or, in the case of an extrusion, e.g. also by means of a vented extruder), a solid or highly viscous or pasty solution of the active substance in the comb polymer being obtained. Suitable solvents for this are essentially those which are capable of dissolving both the active substance and the comb polymer, for example aliphatic nitriles, such as acetonitrile and propionitrile, N,N-dialkylamides of aliphatic carboxylic acids, such as dimethylformamide and dimethylacetamide, N-alkyllactams, such as N-methylpyrrolidone, the abovementioned aliphatic and alicyclic ethers, for example tetrahydrofuran, halogenated hydrocarbons, such as dichloromethane or dichloroethane, ethers of aliphatic $C_1$-$C_4$-carboxylic acids with $C_1$-$C_6$-alkanols, such as ethyl acetate, butyl acetate, butyl formate, methyl propionate or methyl butyrate, and mixtures of the abovementioned solvents. If appropriate, desired additives and auxiliaries can be incorporated in the composition at this point in a way known per se.

This procedure is also suitable in principle for the preparation of solvent-comprising formulations, it then generally being possible to dispense with removal of the solvent or the solvent if appropriate used for the preparation of the homogeneous mixture being replaced by another organic solvent.

The solid active substance formulations according to the invention can also be prepared by drying a liquid formulation according to the invention, in particular by drying an aqueous active substance formulation. For example, the liquid active substance formulations according to the invention, in particular aqueous active substance formulations but also solutions of the active or effect substance and of the comb polymers in an organic solvent, can be dried to give a redispersible solid material, such as, e.g., powders or granules, i.e., by removal of the aqueous phase or of the organic solvent during the drying, finely divided powders or coarsely divided granules are obtained, depending on the drying conditions, which can be dissolved or dispersed without any problem in water without a significant increase in particle size occurring.

Accordingly, a preferred embodiment of the invention relates to solid active substance formulations which are obtained by drying the aqueous active substance formulations. In this connection, solid materials are concerned which are usually obtained in particle form. Depending on the type of the drying process, powders or granules, e.g., are obtained.

For the drying, the volatile constituents, i.e. water and/or organic solvents, are removed using conventional methods. Mention may be made in particular of convective drying methods, such as spray drying, spray fluidized-bed drying, flash drying, mill drying, belt drying and mixed forms of these drying methods, contact drying processes, such as drum drying, oven drying, thin-film drying, drying in a paddle dryer or in a rotary dryer, freeze drying and radiation drying. Such processes are familiar to a person skilled in the art, e.g. from C. M. van't Land, "Industrial Drying Equipment", Marcel Decker Inc., 1991; O. Krischer, W. Kast and K. Kröll, "Trocknungstechnik" [Drying Techniques], Vol. 1 to 3, Springer-Verlag, 1978, 1959 and 1989; K. Masters, Spray Drying Handbook, Longman Scientific and Technical; H. Uhlmann/Lothar Mörl, Wirbelschicht/Sprüh-granulat [Fluidized-bed/spray granules], Springer-Verlag, 2000. The aqueous active substance formulations are preferably dried at temperatures below the glass transition temperature of the comb polymer and in particular in the range from −20° C. to 100° C.

In a second embodiment of the present invention, an aqueous active substance formulation is manufactured by first manufacturing a homogeneous nonaqueous mixture comprising a comb polymer and at least one active substance and/or effect substance and by subsequently dispersing the mixture thus obtained in water or an aqueous medium, for example by applying shear forces, e.g. with stirring or by means of a disperser. With regard to the manufacture of the homogeneous nonaqueous mixture, that which was said previously in connection with the first embodiment for the manufacture of a homogeneous nonaqueous mixture comprising comb polymer and active substance and/or effect substance is analogously valid. Dispersing can be carried out both at temperatures in the region of ambient temperature and at elevated temperature, for example at a temperature ranging from 10 to 80° C. and in particular ranging from 20 to 50° C.

In an additional embodiment of the present invention, the manufacture of the aqueous active substance formulation is carried out by incorporating the active substance and/or effect substance in an aqueous solution/dispersion of the comb polymer. For this, the procedure is generally such that the incorporation is carried out at a temperature lying above the melting point of the active or effect substance and preferably at a temperature at which the active or effect substance melt is of low viscosity, i.e. exhibits a viscosity ranging from 1 to 1000 mPa·s (according to DIN 53019-2 at 25° C.). The incorporation is preferably carried out while applying strong shear forces, for example in an UltraTurrax.

In another embodiment of the invention, the aqueous active substance formulation is manufactured by a process which comprises the following stages a to c:

a) manufacturing a solution of active substance and/or effect substance and, if appropriate, comb polymer in an organic solvent exhibiting a lower boiling point than that of water and b) mixing the solution of the active substance and/or effect substance with water or with an aqueous solution of the comb polymer and c) removing the solvent.

In this connection, it is possible to proceed alternatively so that the solution of the active substance comprises the comb polymer and this solution is mixed with water, or that the solution of the active substance comprises only a part of the comb polymer or no comb polymer and this solution is mixed with an aqueous solution or dispersion of the comb polymer. Mixing can be carried out in suitable stirred vessels, it being possible for either water or the aqueous solution of the comb polymer to be introduced and the solution of the active or effect substance being added thereto or alternatively the solution of the active or effect substance being introduced and the water or the aqueous solution of the comb polymer being added thereto. Subsequently, the organic solvent is completely or partially removed, e.g. by distillation, water being added, if appropriate.

In a preferred alternative form of this embodiment, the active substance solution and the water or the aqueous solution of the comb polymer proceed continuously into a mixing region and the mixture is removed continuously from this, from which mixture the solvent is subsequently completely or partially separated. The mixing region can be organized in any way. In principle, all items of equipment which make possible continuous mixing of liquid streams are suitable for this. Such items of equipment are known, e.g. from Continuous Mixing of Fluids (J.-H. Henzler) in Ullmann's Encyclopedia, 5th ed. on CD-Rom, Wiley-VCH. The mixing regions can be organized as static or dynamic mixers or hybrids thereof. In particular, jet mixers or comparable mixers with nozzles are also suitable as mixing regions. In a preferred embodiment, the mixing region is the item of equipment or a comparable item of equipment described in the "Handbook of Industrial Crystallization" (A. S. Myerson, 1993, Butterworth-Heinemann, page 139, ISBN 0-7506-9155-7).

The ratio by volume of active substance solution to water or aqueous solution of the comb polymer according to the invention can be varied over wide ranges and preferably ranges from 10:1 to 1:20 and in particular ranges from 5:1 to 1:10.

Naturally, the solvent should be suitable for dissolving the comb polymer according to the invention and the active substance in the desired ratios of amounts. Suitable solvents can be determined by a person skilled in the art through routine experiments. Examples of suitable solvents are $C_2$-$C_4$-alkanols, such as ethanol, n-propanol, n-butanol or isobutanol, the abovementioned aliphatic and alicyclic ethers, such as diethyl ether, diisopropyl ether, methyl tert-butyl ether, dioxane or tetrahydrofuran, ketones, such as acetone or methyl ethyl ketone, lactones, such as gamma-butyrolactone, carbonates, such as diethyl carbonate, ethylene carbonate or propylene carbonate, lactams, such as pyrrolidone, N-methylpyrrolidone, N-ethylpyrrolidone or caprolactam, amides of aliphatic carboxylic acids, such as acetamide, N,N-dimethylacetamide or N,N-dimethylformamide, nitriles, such as acetonitrile and propionitrile, halogenated hydrocarbons, such as dichloromethane or dichloroethane, esters of aliphatic $C_1$-$C_4$-carboxylic acids with $C_1$-$C_6$-alkanols, such as ethyl acetate, butyl acetate, butyl formate, methyl propionate, methyl butyrate and the like, and mixtures of the abovementioned organic solvents.

The content of active and/or effect substance can be varied over wide ranges. In particular, the comb polymers make possible the manufacture of "active substance concentrates" which comprise the active substance in an amount of at least 5% by weight, e.g. in an amount of 5 to 50% by weight and in particular in an amount of 5 to 40% by weight, based on the total weight of the formulation.

Advantageously, the formulations according to the invention, in particular the aqueous active substance formulations and the solid or pasty formulations, can be formulated free from solvent or with a low solvent content, i.e. the proportion of volatile organic constituents in the active substance formulations is frequently not more than 10% by weight, in particular not more than 5% by weight and especially not more than 1% by weight, based on the total weight of the formulation. Volatile constituents are, in this connection, those which exhibit a boiling point of less than 200° C. under standard pressure.

A multitude of different active and effect substances can be formulated in the formulations according to the invention. In particular, the comb polymers according to the invention are suitable for the formulations of organic active substances, in particular low molecular weight active substances with a molecular weight of not more than 2000 daltons, in particular not more than 1000 daltons, e.g. in the range from 100 to 1000 daltons and especially in the range from 150 to 500 daltons. A particular embodiment of the invention relates to the formulation of active substances for plant protection, i.e. of herbicides, fungicides, nematicides, acaricides or insecticides, and also active substances which regulate plant growth.

In particular, the active substances used according to the invention are insecticidal and/or fungicidal active substances.

Examples of fungicidal active substances which can be formulated using the comb polymers according to the invention to give an active substance formulation comprise the following organic compounds:

Strobilurins, such as, for example, azoxystrobin, dimoxystrobin, enestroburin, fluoxastrobin, kresoxim-methyl, metominostrobin, picoxystrobin, pyraclostrobin, trifloxystrobin, orysastrobin, methyl(2-chloro-5-[1-(3-methylbenzyloxy-imino)ethyl]benzyl)carbamate, methyl (2-chloro-5-[1-(6-methylpyridin-2-ylmethoxy-imino)ethyl]benzyl)carbamate, methyl 2-(ortho(2,5-dimethylphenyl-oxymethyl)phenyl)-3-methoxyacrylate;

Carboxamides

Carboxanilides, such as, for example, benalaxyl, benodanil, boscalid, carboxin, mepronil, fenfuram, fenhexamide, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-(trifluoromethyl)biphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-carboxamide, N-(2-cyanophenyl)-3,4-dichloroisothiazole-5-carboxamide. Suitable carboxanilides are furthermore benalaxyl-M, bixafen, isotianil, kiralaxyl, tecloftalam, 2-amino-4-methylthiazole-5-carboxanilide, 2-chloro-N-(1,1,3-trimethylindan-4-yl)nicotinamide, N-(3',4'-dichloro-5-fluorobiphenyl-2-yl)-3-difluoromethyl-1-methyl-1H-pyrazole-4-carboxamide, N-(3',4'-dichloro-5-fluorobiphenyl-2-yl)-3-trifluoromethyl-1-methyl-1H-pyrazole-4-carboxamide, N-[2-(1,3-dimethylbutyl)phenyl]-5-fluoro-1,3-dimethyl-1H-pyrazole-4-carboxamide, N-(4'-chloro-3',5-difluorobiphenyl-2-yl)-3-difluoromethyl-1-methyl-1H-pyrazole-4-carboxamide, N-(4'-chloro-3',5-difluorobiphenyl-2-yl)-3-trifluoromethyl-1-methyl-1H-pyrazole-4-carboxamide, N-(3',5-difluoro-4'-methylbiphenyl-2-yl)-3-difluoromethyl-1-methyl-1H-pyrazole-4-carboxamide, N-(3',5-difluoro-4'-methylbiphenyl-2-yl)-3-trifluoromethyl-1-methyl-1H-pyrazole-4-carboxamide, N-[2-(bicyclopropyl-2- yl)phenyl]-3-difluoromethyl-1-methyl-1H-pyrazole-4-carboxamide, N-[2-(cis-bicyclopropyl-2-yl)phenyl]-3-difluoromethyl-1-methyl-1H-pyrazole-4-carboxamide and N-[2-(trans-bicyclopropyl-2-yl)phenyl]-3-difluoromethyl-1-methyl-1H-pyrazole-4-carboxamide;

carboxylic acid morpholides, such as, for example, dimethomorph, flumorph;

benzamides, such as, for example, flumetover, fluopicolide (picobenzamid) zoxamide. Also suitable is N-(3-ethyl-3,5,5-trimethylcyclohexyl)-3-formylamino-2-hydroxybenzamide;

other carboxamides, such as, for example, carpropamid, diclocymet, mandipropamid, N-(2-(4-[3-(4-chlorophenyl)prop-2-ynyloxy]-3-methoxy-phenyl)ethyl)-2-methylsulfonylamino-3-methylbutyramide, N-(2-(4-[3-(4-chlorophenyl)prop-2-ynyloxy]-3-methoxyphenyl)ethyl)-2-ethylsulfonylamino-3-methylbutyramide. Furthermore suitable is oxytetracycline, silthiofam or N-(6-methoxypyridin-3-yl)cyclopropanecarboxamide;

Azoles triazoles, such as, for example, bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;

imidazoles, such as, for example, cyazofamid, imazalil, pefurazoate, prochloraz, triflumizole;

benzimidazoles, such as, for example, benomyl, carbendazim, fuberidazole, thiabendazole; and others, such as ethaboxam, etridiazole, hymexazole;

Nitrogen-Comprising Heterocyclyl Compounds pyridines, such as, for example, fluazinam, pyrifenox, 3-[5-(4-chlorophenyl)-2,3-dimethylisoxazolidin-3-yl]-pyridine;

pyrimidines, such as, for example, bupirimate, cyprodinil, ferimzone, fenarimol, mepanipyrim, nuarimol, pyrimethanil;

piperazines, such as triforine;

pyrroles, such as fludioxonil, fenpiclonil;

morpholines, such as aldimorph, dodemorph, fenpropimorph, tridemorph;

dicarboximides, such as iprodione, procymidone, vinclozolin;

others, such as acibenzolar-S-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 6-aryl-[1,2,4]triazolo[1,5-a]pyrimidines, for example compounds of the formula (IV) defined below, e.g. 5-chloro-7-(4-methylpiperid-1-yl)-6-(2,4,6-trifluorophenyl)-[1,2,4]triazolo[1,5-a]pyrimidine, 2-butoxy-6-iodo-3-propylchromen-4-one, N,N-dimethyl-3-(3-bromo-6-fluoro-2-methylindol-1-sulfonyl)-[1,2,4] triazole-1-sulfonamide;

Carbamates and Dithiocarbamates dithiocarbamates, such as ferbam, mancozeb, maneb, metiram, metam, propineb, thiram, zineb, ziram;

carbamates, such as diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl)ethylsulfonyl)but-2-yl)carbamate;

Other Fungicides guanidines, such as dodine, iminoctadine, guazatine;

antibiotics, such as kasugamycin, polyoxins, streptomycin, validamycin A;

organometallic compounds, such as fentin salts;

sulfur-comprising heterocyclyl compounds, such as isoprothiolane, dithianon;

organophosphorous compounds, such as edifenphos, fosetyl, fosetyl-aluminium, iprobenfos, pyrazophos, tolclofos-methyl, phosphorous acid and its salts;

organochlorine compounds, such as thiophanate-methyl, chlorothalonil, dichlofluanid, tolylfluanid, flusulfamide, phthalide, hexachlorobenzene, pencycuron, quintozene;

nitrophenyl derivatives, such as binapacryl, dinocap, dinobuton;

others, such as, for example, spiroxamine, cyflufenamid, cymoxanil, metrafenon.

Examples of herbicidal active substances which can be formulated using the comb polymers according to the invention to give an active substance formulation comprise:

1,3,4-thiadiazoles, such as buthidazole and cyprazole;

amides, such as allidochlor, benzoylprop-ethyl, bromobutide, chlorthiamid, dimepiperate, dimethenamid, diphenamid, etobenzanid, flamprop-methyl, fosamine, isoxaben, metazachlor, monalide, naptalam, pronamide, propanil;

aminophosphoric acids, such as bilanafos, buminafos, glufosinate-ammonium, glyphosate, sulfosate;

aminotriazoles, such as amitrole, anilides, such as anilofos, mefenacet;

anilides, such as anilofos, mefenacet;

aryloxyalkanoic acid, such as 2,4-D, 2,4-DB, clomeprop, dichlorprop, dichlorprop-P, fenoprop, fluroxypyr, MCPA, MCPB, mecoprop, mecoprop-P, napropamide, naproanilide, triclopyr;

benzoic acids, such as chloramben, dicamba;

benzothiadiazinones, such as bentazon;

bleachers, such as clomazone, diflufenican, fluorochloridone, flupoxam, fluridone, pyrazolate, sulcotrione;

carbamates, such as carbetamide, clorbufam, chlorpropham, desmedipham, phenmedipham, vernolate;

quinolinecarboxylic acids, such as quinclorac, quinmerac;

dichloropropionic acids, such as dalapon;

dihydrobenzofurans, such as ethofumesate;

dhydrofuran-3-ones, such as flurtamone;

dinitroanilines, such as benefin, butralin, dinitramine, ethalfluralin, fluchloralin, isopropalin, nitralin, oryzalin, pendimethalin, prodiamine, profluralin, trifluralin;

dinitrophenols, such as bromofenoxim, dinoseb, dinoseb acetate, dinoterb, DNOC, medinoterb acetate;

diphenyl ethers, such as acifluorfen-sodium, aclonifen, bifenox, chlornitrofen, difenoxuron, ethoxyfen, fluorodifen, fluoroglycofen-ethyl, fomesafen, furyloxyfen, lactofen, nitrofen, nitrofluorfen, oxyfluorfen;

dipyridyls, such as cyperquat, difenzoquat metilsulfate, diquat or paraquat dichloride;

imidazoles, such as isocarbamid;

imidazolinones, such as imazamethapyr, imazapyr, imazaquin, imazamethabenz-methyl, imazethapyr, imazapic, imazamox;

oxadiazoles, such as methazole, oxadiargyl, oxadiazon;

oxiranes, such as tridiphane;

phenols, such as bromoxynil, ioxynil;

phenoxyphenoxypropionic acid esters, such as clodinafop, cyhalofop-butyl, diclofop-methyl, fenoxaprop-ethyl, fenoxaprop-P-ethyl, fenthiaprop-ethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl, quizalofop-tefuryl;

phenylacetic acids, such as chlorfenac;

phenylpropionic acids, such as chlorphenprop-methyl;

ppi-active substances, (ppi=preplant incorporated), such as benzofenap, flumiclorac-pentyl, flumioxazin, flumipropyn, flupropacil, pyrazoxyfen, sulfentrazone, thidiazimin;

pyrazoles, such as nipyraclofen;

pyridazines, such as chloridazon, maleic hydrazide, norflurazon, pyridate;

pyridinecarboxylic acids, such as clopyralid, dithiopyr, picloram, thiazopyr;

pyrimidyl ethers, such as pyrithiobac acid, pyrithiobac-sodium, KIH-2023, KIH-6127;

sulfonamides, such as flumetsulam, metosulam;

triazolecarboxamides, such as triazofenamide;

uracils, such as bromacil, lenacil, terbacil;

furthermore benazolin, benfuresate, bensulide, benzofluor, bentazon, benfuresate, butamifos, cafenstrole, chlorthal-dimethyl, cinmethylin, dichlobenil, endothall, fluorbentranil, mefluidide, perfluidone, piperophos, topramezone and prohexadione-calcium;

sulfonylureas, such as amidosulfuron, azimsulfuron, bensulfuron-methyl, chlorimuron-ethyl, chlorsulfuron, cinosulfuron, cyclosulfamuron, ethametsulfuron-methyl, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron;

plant protection active substances of the cyclohexenone type, such as alloxydim, clethodim, cloproxydim, cycloxydim, sethoxydim and tralkoxydim. Very particularly preferred herbicidal active substances of the cyclohexenone type are: tepraloxydim (cf. AGROW, No. 243, Nov. 3, 1995, page 21, cycloxydim) and 2-(1-[2-{4-chlorphenoxy}propyloxyimino]butyl)-3-hydroxy-5-(2H-tetrahydrothiopyran-3-yl)-2-cyclohexen-1-one, and of the sulfonylurea type is: N-(((4-methoxy-6-[trifluoromethyl]-1,3,5-triazin-2-yl)amino) carbonyl)-2-(trifluoromethyl)benzenesulfonamide.

Examples of insecticides which can be formulated using the comb polymers according to the invention to give an active substance formulation comprise:

organo(thio)phosphates, such as acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isoxathion, malathion, mecarbam, methamidophos, methidathion, methyl-parathion, mevinphos, monocrotophos, naled, omethoate, oxydemeton-methyl, paraoxon, parathion, parathion-methyl, phenthoate, phorate, phosalone, phosmet, phosphamidon, phorate, phoxim, pirimiphos, pirimiphos-methyl, profenofos, propetamphos, prothiofos, pyraclofos, pyridaphenthion, quinalphos, sulfotep, sulprofos, tebupirimfos, temephos, terbufos, tetrachlorvinphos, thiometon, triazophos, trichlorfon, vamidothion;

carbamates, such as alanycarb, aldicarb, bendiocarb, benfuracarb, butocarboxim, butoxycarboxim, carbaryl, carbofuran, carbosulfan, ethiofencarb, fenobucarb, fenoxycarb, formetanate, furathiocarb, isoprocarb, methiocarb, methomyl, metolcarb, oxamyl, pirimicarb, propoxur, thiodicarb, thiofanox, triazamate, trimethacarb, XMC, xylylcarb;

pyrethroids, such as acrinathrin, allethrin, d-cis-trans-allethrin, d-trans-allethrin, bifenthrin, bioallethrin, bioallethrin S-cyclopentenyl, bioresmethrin, cyclopro-thrin, cyfluthrin, beta-cyfluthrin, cyhalothrin, lambda-cyhalothrin, gamma-cyhalothrin, cyphenothrin, cypermethrin, alpha-cypermethrin, beta-cypermethrin, theta-cypermethrin, zeta-cypermethrin, deltamethrin, empenthrin, esfenvalerate, etofenprox, fenpropathrin, fenvalerate, flucythrinate, flumethrin, tau-fluvalinate, halfenprox, imiprothrin, permethrin, phenothrin, pralethrin, profluthrin, pyrethrin I and II, resmethrin, RU 15525, silafluofen, tefluthrin, tetramethrin, tralomethrin, transfluthrin, dimefluthrin, ZXI 8901;

arthropod growth regulators: a) chitin synthesis inhibitors, e.g. benzoylureas, such as bistrifluron, chlorfluazuron, diflubenzuron, flucycloxuron, flufenoxuron, hexaflumuron, lufenuron, novaluron, noviflumuron, teflubenzuron, triflumuron, buprofezin, diofenolan, hexythiazox, etoxazole, clofentezine; b) ecdysone antagonists, such as chromafenozide, halofenozide, methoxyfenozide, tebufenozide, azadirachtin; c) juvenile hormone mimics, such as pyriproxyfen, hydroprene, kinoprene, methoprene, fenoxycarb; d) lipid biosynthesis inhibitors, such as spirodiclofen, spiromesifen, spirotetramat;

nicotine receptor agonists/antagonists: acetamiprid, clothianidin, dinotefuran, imidacloprid, nitenpyram, thiacloprid, thiamethoxam, nicotine, bensultap, cartap hydrochloride, thiocyclam, thiosultap-sodium; the thiazole compound of the formula ($\Gamma^1$)

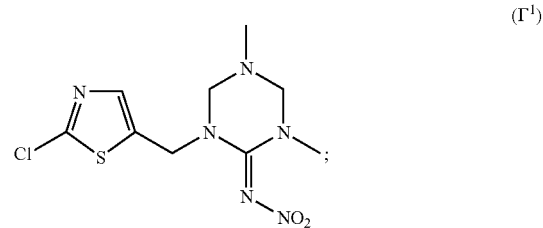 [SMILES: CN1CN(C)/C(=N\[N+](=O)[O-])N(Cc2cnc(Cl)s2)C1]

($\Gamma^1$)

GABA antagonists, such as acetoprole, chlordane, endosulfan, ethiprole, gamma-HCH (lindane), fipronil, vaniliprole, pyrafluprole, pyriprole, phenylpyrazole compounds of the formula $\Gamma^2$

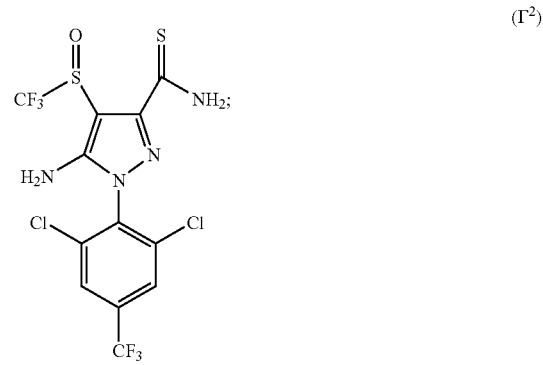 [SMILES: NC(=S)c1nn(-c2c(Cl)cc(C(F)(F)F)cc2Cl)c(N)c1S(=O)C(F)(F)F]

($\Gamma^2$)

macrocyclic lactones, such as abamectin, emamectin, emamectin benzoate, milbemectin, lepimectin, spinosad;

METI I compounds, such as fenazaquin, fenpyroximate, flufenerim, pyridaben, pyrimidifen, rotenone, tebufenpyrad, tolfenpyrad;

METI II and III compounds, such as acequinocyl, fluacrypyrim, hydramethylnon;

uncoupling compounds, such as chlorfenapyr, DNOC;

inhibitors of oxidative phosphorylation, such as azocyclotin, cyhexatin, diafenthiuron, fenbutatin oxide, propargite, tetradifon;

various oxidase inhibitors, such as piperonyl butoxide;

sodium channel blockers, such as indoxacarb, metaflumizone;

microbial disruptors, such as *Bacillus thuringiensis* subsp. *israelensis, Bacillus sphaericus, Bacillus thuringiensis* subsp. *aizawai, Bacillus thuringiensis* subsp. *kurstaki, Bacillus thuringiensis* subsp. *tenebrionis;* additional, such as amitraz, benclothiaz, benzoximate, bifenazate, bromopropylate, cartap, chinomethionat, chloropicrin, flonicamid, methyl bromide, pyridalyl, pymetrozine, rynaxypyr, sulfur, potassium antimonyl tartrate, thiocyclam, tribufos, flubendiamide, cyenopyrafen, flupyrazofos, cyflumetofen, amidoflumet, NNI-0101, N—R'-2,2-dihalo-1-R"-cyclopropanecarboxamide 2-(2,6-dichloro-α,α,α-trifluoro-p-tolyl)hydrazone or N—R'-2,2-di(R"')propionamide 2-(2,6-dichloro-α,α,α-trifluoro-p-tolyl)hydrazone, in which R' is methyl or ethyl, halo is chlorine or bromine, R" is hydrogen or methyl and R"' is methyl or ethyl, anthranilamides of the formula I'³

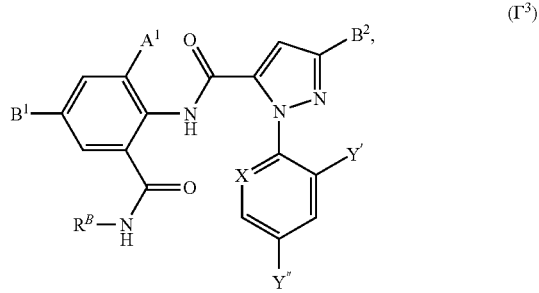

in which A¹ is CH₃, Cl, Br or I, X is C—H, C—Cl, C—F or N, Y' is F, Cl or Br, Y" is F, Cl or CF₃, B¹ is hydrogen, Cl, Br, I or CN, B² is Cl, Br, CF₃, OCH₂CF₃, OCF₂H and R^B is hydrogen, CH₃ or CH(CH₃)₂, and malononitriles, such as disclosed in JP 2002 284608, WO 02/89579, WO 02/90320, WO 02/90321, WO 04/06677, WO 04/20399 or JP 2004 99597;

malonodinitriles, such as CF₃(CH₂)₂C(CN)₂CH₂(CF₂)₃CF₂H, CF₃(CH₂)₂C(CN)₂CH₂(CF₂)₅CF₂H, CF₃(CH₂)₂ C(CN)₂(CH₂)₂C(CF₃)₂F, CF₃(CH₂)₂C(CN)₂(CH₂)₂(CF₂)₃CF₃, CF₂H(CF₂)₃CH₂C(CN)₂CH₂(CF₂)₃CF₂H, CF₃(CH₂)₂C(CN)₂CH₂(CF₂)₃CF₃, CF₃(CF₂)₂CH₂C(CN)₂CH₂(CF₂)₃CF₂H, CF₃CF₂CH₂C(CN)₂CH₂(CF₂)₃CF₂H, 2-(2,2,3,3,4,4,5,5-octafluoropentyl)-2-(3,3,4,4,4-pentafluorobutyl)malononitrile and CF₂HCF₂CF₂CF₂CH₂C(CN)₂ CH₂CH₂CF₂CF₃;

fluorinated quinazolinones, such as:

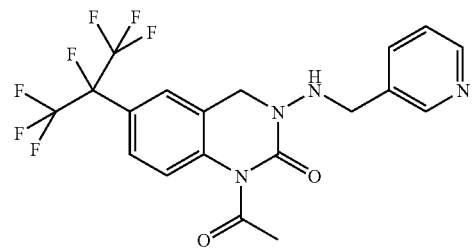 [SMILES: CC(=O)N1C(=O)N(NCc2cccnc2)Cc2cc(C(F)(C(F)(F)F)C(F)(F)F)ccc21]

1-acetyl-3-[(pyridin-3-ylmethyl)amino]-6-(1,2,2,2-tetrafluoro-1-(trifluoromethyl)ethyl)-3,4-dihydro-1H-quinazolin-2-one;

in addition, pyrimidinyl alkynyl ethers of the formula I'⁴ or thiadiazolyl alkynyl ethers of the formula I'⁵:

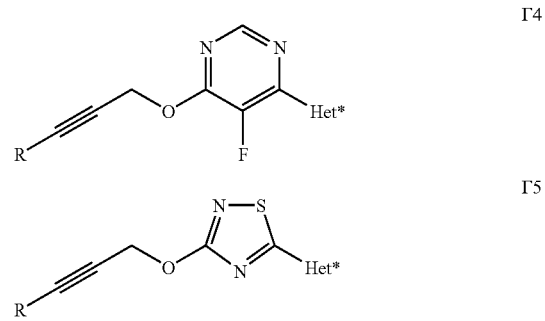

in which R is methyl or ethyl and Het* is 3,3-dimethylpyrrolidin-1-yl, 3-methylpiperidin-1-yl, 3,5-dimethylpiperidin-1-yl, 4-methylpiperidin-1-yl, hexahydroazepin-1-yl, 2,6-dimethylhexahydroazepin-1-yl or 2,6-dimethylmorpholin-4-yl. These compounds are disclosed, for example, in JP 2006 131529.

A preferred embodiment of the invention relates to the use of the comb polymers according to the invention for the manufacture of active substance formulations of fungicides which are insoluble or sparingly soluble in water or use of the comb polymers according to the invention for the solubilization in an aqueous medium of fungicides which are insoluble or sparingly soluble in water.

In a preferred embodiment, the formulated active substance is chosen from strobilurins, e.g. azoxystrobin, dimoxystrobin, fluoxastrobin, kresoxim-methyl, metominostrobin, orysastrobin, picoxystrobin, pyraclostrobin and trifloxystrobin, especially pyraclostrobin, conazole fungicides, in particular prochloraz, cyproconazole, epoxiconazole, fluquinconazole, hexaconazole, metconazole, penconazole, propiconazole, prothioconazole, tebuconazole and triticonazole, and especially epoxiconazole, metconazole, fluquinconazole or prothioconazole, 6-aryl-[1,2,4]triazolo[1,5-a]pyrimidines, in particular from active substances of the general formula (IV) as defined below, and active substances of the general formula IV

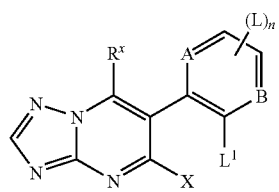

(IV)

mixtures of these active substances.

In formula IV, the variables have the following meanings:

$R^x$ is chosen from $NR^{14}R^{15}$, optionally substituted $C_1$-$C_8$-alkyl, $C_2$-$C_6$-alkenyl, $C_3$-$C_6$-cycloalkyl, $C_3$-$C_6$-cycloalkenyl, phenyl or naphthyl, it being possible for the last 4 radicals mentioned to be optionally substituted;

$R^{14}$, $R^{15}$ are, independently of one another, chosen from hydrogen, $C_1$-$C_8$-alkyl, $C_1$-$C_8$-haloalkyl, $C_3$-$C_{10}$-cycloalkyl, $C_3$-$C_6$-halocycloalkyl, $C_2$-$C_8$-alkenyl, $C_4$-$C_{10}$-alkadienyl, $C_2$-$C_8$-haloalkenyl, $C_3$-$C_6$-cycloalkenyl, $C_2$-$C_8$-halocycloalkenyl, $C_2$-$C_8$-alkynyl, $C_2$-$C_8$-haloalkynyl or $C_3$-$C_6$-cycloalkynyl; or $R^{14}$ together with $R^{15}$ and the nitrogen atom to which they are bonded are a five- to eight-membered heterocyclyl which is bonded via N and comprises, if appropriate, 1, 2 or 3 additional heteroatoms from the group consisting of O, N and S as ring member and is optionally substituted;

n is 1, 2, 3 or 4;

A is CH, C-L or N;

B is CH, C-L or N;

L is or are, independently of one another, chosen from halogen, cyano, $C_1$-$C_6$-alkyl, $C_1$-$C_4$-haloalkyl, $C_1$-$C_6$-alkoxy, $C_1$-$C_4$-haloalkoxy and $C_1$-$C_6$-alkoxycarbonyl;

$L^1$ is chosen from hydrogen, halogen, $C_1$-$C_6$-alkyl and $C_1$-$C_6$-haloalkyl;

X is chosen from halogen, $C_1$-$C_4$-alkyl, cyano, $C_1$-$C_4$-alkoxy or $C_1$-$C_4$-haloalkyl.

Particularly preferred examples of compounds of the formula IV are 5-chloro-7-(4-methylpiperidin-1-yl)-6-(2,4,6-trifluorophenyl)-[1,2,4]triazolo[1,5-a]pyrimidine, 6-(3,4-dichlorophenyl)-5-methyl-[1,2,4]triazolo[1,5-a]pyrimidin-7-ylamine, 6-(4-(tert-butyl)phenyl)-5-methyl-[1,2,4]triazolo[1,5-a]pyrimidin-7-ylamine, 5-methyl-6-(3,5,5-trimethylhexyl)-[1,2,4]triazolo[1,5-a]pyrimidin-7-ylamine, 5-methyl-6-octyl-[1,2,4]triazolo[1,5-a]pyrimidin-7-ylamine, 5-ethyl-6-octyl-[1,2,4]triazolo[1,5-a]pyrimidine-2,7-diamine, 6-ethyl-5-octyl-[1,2,4]triazolo[1,5-a]pyrimidin-7-ylamine, 5-ethyl-6-octyl-[1,2,4]triazolo[1,5-a]pyrimidin-7-ylamine, 5-ethyl-6-(3,5,5-trimethylhexyl)-[1,2,4]triazolo[1,5-a]pyrimidin-7-ylamine, 6-octyl-5-propyl-[1,2,4]triazolo[1,5-a]pyrimidin-7-ylamine, 5-methoxymethyl-6-octyl-[1,2,4]triazolo[1,5-a]pyrimidin-7-ylamine, 6-octyl-5-trifluoromethyl-[1,2,4]triazolo[1,5-a]pyrimidin-7-ylamine, 5-trifluoromethyl-6-(3,5,5-trimethylhexyl)-[1,2,4]triazolo[1,5-a]pyrimidin-7-ylamine and the agriculturally suitable salts thereof.

In an additional embodiment of the active substance formulations according to the invention, these comprise a combination of at least two active substances, in particular of at least two fungicides. Specifically, the active substance combination is a combination of at least one conazole fungicide, especially epoxiconazole, with at least one strobilurin, in particular pyraclostrobin, and, if appropriate, an additional active substance, e.g. fenpropidin; a combination of two different conazole fungicides, especially epoxiconazole with at least one additional conazole fungicide other than epoxiconazole, in particular with a conazole fungicide chosen from prochloraz, cyproconazole, fluquinconazole, hexaconazole, metconazole, penconazole, propiconazole, prothioconazole, tebuconazole and triticonazole and especially metconazole, fluquinconazole and prothioconazole; and a combination of at least one 6-aryl-[1,2,4]triazolo[1,5-a]pyrimidine, in particular an active substance of the general formula (IV), especially 5-chloro-7-(4-methylpiperidin-1-yl)-6-(2,4,6-trifluorophenyl)-[1,2,4]triazolo[1,5-a]pyrimidine, with at least one other fungicidal active substance, especially with one or more conazole fungicides.

An additional preferred embodiment of the invention relates to the use of the comb polymers according to the invention for the manufacture of active substance formulations of insecticides, in particular of arylpyrroles, such as chlorfenapyr, of pyrethroids, such as bifenthrin, cyfluthrin, cycloprothrin, cypermethrin, deltamethrin, esfenvalerate, etofenprox, fenpropathrin, fenvalerate, cyhalothrin, lambda-cyhalothrin, permethrin, silafluofen, tau-fluvalinate, tefluthrin, tralomethrin, alpha-cypermethrin and zeta-cypermethrin and permethrin, of neonicotinoids and of semicarbazones, such as metaflumizone.

A preferred embodiment of the invention accordingly also relates to the use of the comb polymers according to the invention for the stabilization or solubilization of insecticides, in particular of arylpyrroles, of pyrethroids, of neonicotinoids and of metaflumizone, in an aqueous phase.

In addition, the comb polymers according to the invention are suitable for the manufacture of active substance formulations, in particular aqueous active substance formulations, of pharmaceutical active substances and prodrugs. These include benzodiazepines, antihypertensives, vitamins, cytostatics, in particular taxol, anesthetics, neuroleptics, antidepressants, antibiotics, antimycotics, fungicides, chemotherapeutics, urologics, thrombocyte aggregation inhibitors, sulfonamides, spasmolytics, hormones, immunoglobulins, sera, thyroid therapeutic agents, psychopharmacological agents, antiparkinsonians and other antihyperkinetic agents, ophthalmics, neuropathy preparations, calcium metabolism regulators, muscle relaxants, narcotics, antilipemics, hepatic therapeutic agents, coronary agents, cardiacs, immunotherapeutics, regulatory peptides and their inhibitors, hypnotics, sedatives, gynecological agents, antigouts, fibrinolytic agents, enzyme preparations and transport proteins, enzyme inhibitors, emetics, circulation-promoting agents, diuretics, diagnostics, corticoids, cholinergics, bile duct therapeutics, antiasthmatics, broncholytics, beta-receptor blockers, calcium antagonists, ACE inhibitors, antiarteriosclerotics, antiinflammatories, anticoagulants, antihypotensives, antihypoglycemics, antihypertonics, antifibrinolytics, antiepileptics, antiemetics, antidotes, antidiabetics, antiarrhythmics, antianemics, antiallergics, anthelmintics, analgesics, analeptics, aldosterone antagonists and slimming agents. Examples of suitable pharmaceutical active substances are in particular the active substances mentioned in paragraphs 0105 to 0131 of US 2003/0157170.

Furthermore, the comb polymers according to the invention are suitable for the manufacture of formulations, in particular aqueous formulations of cosmetic active substances, in particular of cosmetic oils and fats, such as peanut oil, jojoba oil, coconut oil, almond oil, olive oil, palm oil, castor oil, soybean oil or wheat germ oil, essential oils, such as mountain pine oil, lavender oil, rosemary oil, spruce needle oil, pine needle oil, eucalyptus oil, peppermint oil, sage oil, bergamot oil, turpentine oil, Melissa oil, juniper oil, lemon oil, anise oil, cardamom oil, camphor oil, and the like, or for mixtures of these oils.

In addition, the comb polymers according to the invention are suitable for the manufacture of formulations, in particular aqueous formulations of food supplements, such as water-insoluble vitamins and provitamins, such as vitamin A, vitamin A acetate, vitamin D, vitamin E, tocopherol derivatives, such as tocopherol acetate, coenzyme Q10 and vitamin K.

Accordingly, the comb polymers according to the invention are also suitable for the stabilization of the abovementioned active substances in an aqueous phase.

Examples of effect substances which can be formulated as active substance formulation according to the invention are:

Dyes: e.g., the dyes disclosed in DE-A 10245209 and the compounds described, according to the Colour Index, as disperse dyes and as solvent dyes, which are also described as dispersion dyes. A list of suitable dispersion dyes is found, for example, in Ullmann's Encyclopedia of Industrial Chemistry, 4th edition, Vol. 10, pp. 155-165 (see also Vol. 7, p. 585ff—Anthraquinone Dyes; Vol. 8, p. 244ff—Azo Dyes; Vol. 9, p. 313ff—Quinophthalone Dyes). Particular reference is made herewith to this literature reference and to the compounds mentioned therein. Suitable dispersion dyes and solvent dyes according to the invention comprise the most varied categories of dyes with various chromophores, for example anthraquinone dyes, monoazo and disazo dyes, quinophthalone dyes, methine and azamethine dyes, naphthalimide dyes, naphthoquinone dyes and nitro dyes. Examples of suitable dispersion dyes according to the invention are the dispersion dyes of the following Colour Index list: C. I. Disperse Yellow 1—228, C. I. Disperse Orange 1—148, C. I. Disperse Red 1—349, C. I. Disperse Violet 1—97, C. I. Disperse Blue 1—349, C. I. Disperse Green 1—9, C. I. Disperse Brown 1—21, C. I. Disperse Black 1—36. Examples of suitable solvent dyes according to the invention are the compounds of the following Colour Index list: C. I. Solvent Yellow 2—191, C. I. Solvent Orange 1—113, C. I. Solvent Red 1—248, C. I. Solvent Violet 2—61, C. I. Solvent Blue 2—143, C. I. Solvent Green 1—35, C. I. Solvent Brown 1—63, C. I. Solvent Black 3—50. Suitable dyes according to the invention are furthermore derivatives of naphthalene, of anthracene, of perylene, of terylene or of quarterylene, and diketopyrrolopyrrole dyes, perinone dyes, coumarin dyes, isoindoline and isoindolinone dyes, porphyrin dyes, and phthalocyanine and naphthalocyanine dyes; and UV absorbers: and in particular compounds from the groups a to g mentioned below:

a) 4,4-diarylbutadienes, b) cinnamates, c) benzotriazoles, d) hydroxybenzophenones, e) diphenylcyanoacrylates, f) oxamides, g) 2-phenyl-1,3,5-triazines.

The group a) of 4,4-diarylbutadienes includes, for example, compounds of the formula A.

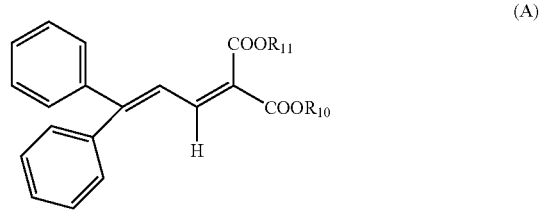

(A)

The compounds are known from EP-A-916 335. The $R_{10}$ and/or $R_{11}$ substituents preferably represent $C_1$-$C_8$-alkyl and $C_5$-$C_8$-cycloalkyl.

The group b) of the cinnamates includes, for example, 2-isoamyl 4-methoxycinnamate, 2-ethylhexyl 4-methoxycinnamate, methyl α-(methoxycarbonyl)cinnamate, methyl α-cyano-β-methyl-p-methoxycinnamate, butyl α-cyano-β-methyl-p-methoxycinnamate and methyl α-(methoxycarbonyl)-p-methoxycinnamate.

The group c) of the benzotriazoles includes, for example, 2-(2'-hydroxyphenyl)benzotriazoles, such as 2-(2'-hydroxy-5'-methylphenyl)benzotriazole, 2-(3',5'-di(tert-butyl)-2'-hydroxyphenyl)benzotriazole, 2-(5'-(tert-butyl)-2'-hydroxyphenyl)benzotriazole, 2-(2'-hydroxy-5'-(1,1,3,3-tetramethylbutyl)phenyl)benzotriazole, 2-(3',5'-di(tert-butyl)-2'-hydroxyphenyl)-5-chlorobenzotriazole, 2-(3'-(tert-butyl)-2'-hydroxy-5'-methylphenyl)-5-chlorobenzotriazole, 2-(3'-(sec-butyl)-5'-(tert-butyl)-2'-hydroxyphenyl)benzotriazole, 2-(2'-hydroxy-4'-octyloxyphenyl)benzotriazole, 2-(3',5'-di(tert-amyl)-2'-hydroxyphenyl)benzotriazole, 2-(3',5'-bis(α,α-dimethylbenzyl)-2'-hydroxyphenyl)benzotriazole, 2-(3'-(tert-butyl)-2'-hydroxy-5'-(2-octyloxycarbonylethyl)phenyl)-5-chlorobenzotriazole, 2-(3'-(tert-butyl)-5'-[2-(2-ethylhexyloxycarbonyl)ethyl]-2'-hydroxyphenyl)-5-chlorobenzotriazole, 2-(3'-(tert-butyl)-2'-hydroxy-5'-(2-methoxycarbonylethyl)phenyl)-5-chlorobenzotriazole, 2-(3'-(tert-butyl)-2'-hydroxy-5'-(2-methoxycarbonylethyl)phenyl)benzotriazole, 2-(3'-(tert-butyl)-2'-hydroxy-5'-(2-octyloxycarbonylethyl)phenyl)benzotriazole, 2-(3'-(tert-butyl)-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-(tert-butyl)-2'-hydroxy-5'-(2-isooctyloxy-carbonylethyl)phenyl)benzotriazole, 2,2'-methylenebis[4-(1,1,3,3-tetramethylbutyl)-6-(benzotriazol-2-yl)phenol], the product of the esterification of 2-[3'-(tert-butyl)-5'-(2-methoxycarbonylethyl)-2'-hydroxyphenyl]-2H-benzotriazole with polyethylene glycol 300, [R—$CH_2CH_2$—COO($CH_2$)$_3$]$_2$ with R=3'-(tert-butyl)-4'-hydroxy-5'-(2H-benzotriazol-2-yl)phenyl, and mixtures thereof.

The group d) of the hydroxybenzophenones includes, for example, 2-hydroxybenzophenones, such as 2-hydroxy-4-methoxybenzophenone, 2,2'-dihydroxy-4-methoxybenzophenone, 2,4-dihydroxybenzophenone, 2,2',4,4'-tetra-hydroxybenzophenone, 2,2'-dihydroxy-4,4'-dimethoxybenzophenone, 2,2'-dihydroxy-4,4'-dimethoxybenzophenone, 2-hydroxy-4-(2-ethylhexyloxy)benzophenone, 2-hydroxy-4-(n-octyloxy)benzophenone, 2-hydroxy-4-methoxy-4'-methylbenzophenone, 2-hydroxy-3-carboxybenzophenone, 2-hydroxy-4-methoxybenzophenone-5-sulfonic acid and the sodium salt thereof, and 2,2'-dihydroxy-4,4'-dimethoxybenzophenone-5,5'-disulfonic acid and the sodium salt thereof.

The group e) of the diphenylcyanoacrylates includes, for example, ethyl 2-cyano-3,3-diphenylacrylate, which is available, for example, commercially under the name Uvinul® 3035 from BASF AG, Ludwigshafen, 2-ethylhexyl 2-cyano-3,3-diphenylacrylate, which is available, for example, commercially as Uvinul® 3039 from BASF AG, Ludwigshafen, and 1,3-bis[(2'-cyano-3',3'-diphenylacryloyl)oxy]-2,2-bis{[(2'-cyano-3',3'-diphenylacryloyl)oxy]methyl}propane, which is available, for example, commercially under the name Uvinul® 3030 from BASF AG, Ludwigshafen.

The group f) of the oxamides includes, for example, 4,4'-dioctyloxyoxanilide, 2,2'-di-ethoxyoxanilide, 2,2'-dioctyloxy-5,5'-di(tert-butyl)oxanilide, 2,2'-didodecyloxy-5,5'-di(tert-butyl)oxanilide, 2-ethoxy-2'-ethyloxanilide, N,N'-bis(3-dimethylaminopropyl)-oxamide, 2-ethoxy-5-(tert-butyl)-2'-ethyloxanilide and the mixture thereof with 2-ethoxy-2'-ethyl-5,4'-di(tert-butyl)oxanilide, and also mixtures of ortho- and para-methoxy-disubstituted oxanilides and mixtures of ortho- and para-ethoxy-disubstituted oxanilides.

The group g) of the 2-phenyl-1,3,5-triazines includes, for example, 2-(2-hydroxyphenyl)-1,3,5-triazines, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-(butyloxy)propoxy)phenyl]-4,6-bis(2,4-dimethylphenyl)-1,3,5-triazine, 2-[2-hydroxy-4-(2-hydroxy-3-(octyloxy)propoxy)phenyl]-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-(dodecyloxy)propoxy)phenyl]-4,6-bis(2,4-dimethylphenyl)-1,3,5-triazine, 2-(2-hydroxy-4-hexyloxyphenyl)-4,6-diphenyl-1, 3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine and 2-(2-hydroxyphenyl)-4-(4-methoxyphenyl)-6-phenyl-1,3,5-triazine.

The compositions according to the invention can be formulated in solid form or in liquid form. Depending on the embodiment, the compositions according to the invention can also comprise auxiliaries and/or carriers, such as those which are standard in plant protection compositions or in compositions for material protection. The auxiliaries include in particular conventional surface-active substances and other additives and carriers which are standard in plant protection and material protection, it being possible for these to be solid or liquid. The surface-active substances include in particular surfactants, in particular those which have wetting properties. The other auxiliaries (additives) include in particular thickeners, antifoam agents, preservatives, antifreeze agents, stabilizers, anticaking agents, or free-flow aids, and buffers.

Conventional surface-active substances which can be used in principle are anionic, nonionic and amphoteric surfactants, including polymer surfactants, where the molecular weight of these surfactants will typically not exceed a value of 2000 daltons and in particular 1000 daltons (number-average).

The anionic surfactants include, for example, carboxylates, in particular alkali metal, alkaline earth metal and ammonium salts of fatty acids, e.g. potassium stearate, which are usually also described as soaps; acyl glutamates; sarcosinates, e.g. sodium lauroyl sarcosinate; taurates; methylcelluloses; alkyl phosphates, in particular mono- and diphosphoric acid alkyl esters; sulfates, in particular alkyl sulfates and alkyl ether sulfates; sulphonates, other alkyl- and alkylarylsulfonates, in particular alkali metal, alkaline earth metal and ammonium salts of arylsulfonic acids and alkyl-substituted arylsulfonic acids, alkylbenzenesulfonic acids, such as, for example, lignin- and phenolsulfonic acid, naphthalene- and dibutylnaphthalenesulfonic acids, or dodecylbenzenesulfonates, alkylnaphthalenesulfonates, alkyl methyl ester sulfonates, condensation products of sulfonated naphthalene and derivatives thereof with formaldehyde, condensation products of naphthalenesulfonic acids, phenol- and/or phenolsulfonic acids with formaldehyde or with formaldehyde and urea, or mono- or dialkylsuccinic acid ester sulfonates; and protein hydrolysates and lignosulfite waste liquors. The abovementioned sulfonic acids are advantageously used in the form of their neutral or, if appropriate, basic salts.

The nonionic surfactants include, for example:
fatty alcohol alkoxylates and oxo alcohol alkoxylates, in particular ethoxylates and propoxylates with degrees of alkoxylation of usually 2 to 100 and in particular 3 to 50, e.g. alkoxylates of $C_8$-$C_{30}$-alkanols or alk(adi)enols, e.g. of isotridecyl alcohol, lauryl alcohol, oleyl alcohol or stearyl alcohol, and the $C_1$-$C_4$-alkyl ethers and $C_1$-$C_4$-alkyl esters thereof, e.g. the acetates thereof;
alkoxylated animal and/or vegetable fats and/or oils, for example corn oil ethoxylates, castor oil ethoxylates or tallow fat ethoxylates,
glycerol esters, such as, for example, glycerol monostearate,
alkylphenol alkoxylates, such as, for example, ethoxylated isooctyl-, octyl- or nonylphenol, or tributylphenol polyoxyethylene ethers,
fatty amine alkoxylates, fatty acid amide alkoxylates and fatty acid diethanol-amide alkoxylates, in particular the ethoxylates thereof,
sugar surfactants, sorbitol esters, such as, for example, sorbitan fatty acid esters (sorbitan monooleate, sorbitan tristearate), polyoxyethylene sorbitan fatty acid esters, alkylpolyglycosides or N-alkylgluconamides,
alkyl methyl sulfoxides,
alkyldimethylphosphine oxides, such as, for example, tetradecyldimethylphosphine oxide.

The amphoteric surfactants include, for example, sulfobetaines, carboxybetaines and alkyldimethylamine oxides, e.g. tetradecyidimethylamine oxide.

Additional surfactants which should be mentioned here by way of example are perfluorinated surfactants, silicone surfactants, phospholipids, such as, for example, lecithin or chemically modified lecithins, or amino acid surfactants, e.g. N-lauroyl glutamate.

Unless otherwise specified, the alkyl chains of the abovementioned surfactants are linear or branched radicals with usually 6 to 30 and in particular 8 to 20 carbon atoms.

In one embodiment, the aqueous compositions according to the invention comprise not more than 10% by weight, preferably not more than 5% by weight and in particular not more than 3% by weight, e.g. 0.01 to 5% by weight or 0.1 to 3% by weight, of conventional surface-active substances, each time based on the total amount of active substance and comb polymer.

However, depending on the use, it may be advantageous for the active substance formulations according to the invention to be formulated with surface-active substances. The proportion of conventional surface-active substance then frequently lies in the range from 0.1 to 60% by weight, in particular in the range from 0.5 to 50% by weight, based on the total amount of active substance and comb polymer, or in the range from 0.1 to 60% by weight, in particular in the range from 0.5 to 50% by weight and especially in the range from 0.5 to 30% by weight, based on the total weight of the formulation formulated.

Even if one advantage of the compositions according to the invention is their low content of volatile organic substances, it may for some applications be desirable for the compositions according to the invention to be mixed with organic solvents, oils and fats, preferably those solvents or oils and fats which are environmentally friendly or biocompatible, e.g. the abovementioned water-miscible solvents or solvents, oils or fats which are immiscible with water or only miscible with water to a very limited extent. These include, e.g.:

- paraffin oils, aromatic hydrocarbons and aromatic hydrocarbon mixtures, e.g. xylenes, Solvesso 100, 150 or 200, and the like,
- phenols and alkylphenols, e.g. phenol, hydroquinone, nonylphenol, and the like.
- ketones with more than 4 carbon atoms, such as cyclohexanone, isophorone, isopherone, acetophenone or acetonaphthone,
- alcohols with more than 4 carbon atoms, such as acetylated lanolin alcohol, cetyl alcohol, 1-decanol, 1-heptanol, 1-hexanol, isooctadecanol, isopropyl alcohol, oleyl alcohol or benzyl alcohol,
- carboxylic acid esters, e.g. adipic acid dialkyl esters, such as bis(2-ethylhexyl)adipate, phthalic acid dialkyl esters, such as bis(2-ethylhexyl)phthalate, acetic acid alkyl esters (also branched alkyl groups), such as ethyl acetate and ethyl acetoacetate, stearates, such as butyl stearate or glycerol monostearate, citrates, such as tributyl acetylcitrate, in addition cetyl octanoate, methyl oleate, methyl p-hydroxybenzoate, methyl tetradecanoate, propyl p-hydroxybenzoate, methyl benzoate, or lactic acid esters, such as isopropyl lactate, butyl lactate and 2-ethylhexyl lactate,
- vegetable oils, such as palm oil, rapeseed oil, ricinus oil and derivatives thereof, such as, e.g. oxidized, coconut oil, cod liver oil, corn oil, soybean oil, linseed oil, olive oil, peanut oil, safflower oil, sesame seed oil, grapefruit oil, basil oil, apricot kernel oil, ginger oil, geranium oil, orange oil, rosemary oil, macadamia oil, onion oil, mandarin oil, tall oil or sunflower oil,
- hydrogenated vegetable oils, such as hydrogenated palm oil, hydrogenated rapeseed oil or hydrogenated soybean oil,
- animal oils, such as lard oil or fish oils,
- dialkylamides of medium- to long-chain fatty acids, e.g. hallcomides, and
- vegetable oil esters, such as rapeseed oil methyl ester.

Suitable thickeners are compounds which bestow a pseudoplastic flow behavior on aqueous compositions, i.e. high viscosity at rest and low viscosity in the agitated state. Mention may be made, in this connection, for example, of polysaccharides, such as xanthan (Kelzan® from Kelco; Rhodopol® 23 from Rhône-Poulenc; or Veegum® from R.T. Vanderbilt), and also inorganic layered minerals, such as Attaclay® (Engelhardt), xanthan preferably being used.

Silicone emulsions (such as, e.g., Silicone® SRE, from Wacker, or Rhodorsil® from Rhodia), long-chain alcohols, fatty acids, fluoroorganic compounds and the mixtures thereof, for example, come into consideration as antifoam agents suitable for the dispersions according to the invention.

Bactericides can be added for the stabilization of the compositions according to the invention against infection by microorganisms. In this connection, they are typically isothiazolone compounds, e.g. 1,2-benzisothiazolin-3-one, 5-chloro-2-methylisothiazol-3-one, 2-methylisothiazole-3-one or 2-octylisothiazol-3-one, which can be obtained, for example, under the trade names Proxel® from Arch Chemical Inc., Acticide® RS from Thor Chemie and Kathon® MK from Rohm & Haas.

Suitable antifreeze agents are organic polyols, e.g. ethylene glycol, propylene glycol or glycerol. These are used in aqueous formulations, usually in amounts of not more than 20% by weight, e.g. 1 to 20% by weight and in particular 2 to 10% by weight, based on the total weight of the aqueous active substance formulation.

If appropriate, the active substance formulations according to the invention can, to regulate the pH of the formulation or of the diluted application form, comprise from 1 to 5% by weight of buffer, based on the total amount of the formulation manufactured, the amount and type of the buffer used depending on the chemical properties and the amount of the active substances and of the comb polymer. Examples of buffers are alkali metal salts of weak inorganic or organic acids, such as, e.g., phosphoric acid, boric acid, acetic acid, propionic acid, citric acid, fumaric acid, tartaric acid, oxalic acid and succinic acid.

Examples of free-flow aids are in particular silica, especially pyrogenic silica and precipitated silica, and also calcium carbonate and magnesium stearate. The amount of free-flow aid is, if present, typically up to 5% by weight, in particular up to 2% by weight, e.g. from 0.1 to 5% by weight or from 0.2 to 2% by weight, based on the total weight of the composition.

All liquid and solid substances which are used conventionally in formulations for plant protection or material protection, in particular in formulations of fungicides, and which are typically chemically inert are suitable in principle as carriers. Liquid carriers are in particular water and also mixtures of water with organic water-miscible solvents. Solid carriers are, e.g., silicates and aluminosilicates, including bole, loess, clays and aluminas, e.g. phyllosilicates and tectosilicates, such as montmorillonite, hectorite, saponite, beidellite, sauconite, bentonite, talc, kaolin, attapulgite, furthermore amorphous silicates and silicas, such as silica gels, kieselguhr, e.g. in the form of diatomaceous earth, precipitated silica, synthetic silicates and aluminosilicates, such as zeolites, furthermore limestone, lime, chalk, dolomite, calcium sulfate, magnesium sulfate, magnesium oxide, ground synthetic materials, fertilizers, such as, e.g. ammonium sulfate, ammonium phosphate, ammonium nitrate or ureas, and plant products, such as cereal meal, tree bark meal, wood meal and nutshell meal, cellulose powders and other solid carriers. Preferably, the solid carriers are soluble or dispersible in water.

Depending on the type of the active substance or effect substance present, the active substance or effect substance formulations according to the invention can be used in a way comparable per se to conventional formulations of the respective active or effect substance. For example, active substance formulations comprising at least one insecticidal, acaricidal or nematicidal active substance can be used for the combating of harmful arthropods, e.g. insects or acarids or nematodes. If the active substance formulations according to the invention comprise at least one fungicidal active substance, they can be used for the combating of harmful fungi. If the active substance formulations according to the invention comprise a herbicidal active substance, they can be used for the combating of grass weeds and the like.

Depending on the type of the active substance, the compositions according to the invention are used in particular for the protection of plants from attack by harmful organisms, such as insects, acarids or nematodes, or for protecting from infection by phytopathogenic fungi and the like, or in seed treatment or material protection, for example for the protection of lignocellulose materials, such as wood, from attack by harmful insects, such as wood-destroying beetles, termites, ants and the like, or from infection by wood-discoloring or wood-destroying fungi.

Of course, the compositions according to the invention can also be used in cosmetics or in medicine or in industrial applications.

The following examples serve to illustrate the invention and are not to be understood as limiting.

Analysis:

The glass transition temperature was determined using a DSC apparatus DSC30 from Mettler and a heating rate of 10K/min.

The molecular weights were determined by gel permeation chromatography (Series 1100 apparatus from Agilent) using an RI detector and a 5 μm Mixed-D column from PL at 30° C. (column temperature). Dimethylformamide comprising 0.5% of lithium bromide was used as eluent. The flow rate was 1 ml/min. Calibration was carried out using polymethyl methacrylate calibration sets.

Manufacture of the Comb Polymers

In manufacturing examples 1 to 6, use was made of an ester of methacrylic acid with a methyl polyethylene glycol (subsequently polyethylene glycol methyl ether methacrylate), the ester having exhibited a molecular weight (number-average) of 1100 daltons. This corresponds on average to approximately 23 ethylene oxide repeat units in the polyether chain.

MANUFACTURING EXAMPLES 1-3

General Manufacturing Procedure 1

15 ml of dimethylformamide (DMF) per reaction vessel were placed in a AutoPlant A100 synthesis reactor from Chemspeed® and heated to 95° C. The following were metered into this in parallel with stirring and while maintaining the temperature: feed 1, in 180 min, and, starting simultaneously with feed 1, feed 2, in 195 min. After the feeds had finished being run in, postpolymerization was carried out at 95° C. for a further 60 min.

Manufacturing Example 1

Comb Polymer K1

Feed 1: Mixture consisting of 7.0 g of methyl methacrylate, 3.5 g of n-butyl acrylate and 10.5 g of polyethylene glycol methyl ether methacrylate, dissolved in DMF for 49 ml.

Feed 2: 0.63 g of 2,2'-azobis(2-methylpropionitrile), dissolved in DMF for 6 ml.

Manufacturing Example 2

Comb Polymer K2

Feed 1: Mixture consisting of 3.5 g of lauryl acrylate, 7.0 g of methyl methacrylate and 10.5 g of polyethylene glycol methyl ether methacrylate, dissolved in DMF for 49 ml.

Feed 2: 0.63 g of 2,2'-azobis(2-methylpropionitrile), dissolved in DMF for 6 ml.

Manufacturing Example 3

Comb Polymer K3

Feed 1: Mixture consisting of 14.0 g of methyl methacrylate and 7.0 g of polyethylene glycol methyl ether methacrylate, dissolved in DMF for 49 ml.

Feed 2: 0.63 g of 2,2'-azobis(2-methylpropionitrile), dissolved in DMF for 6 ml.

MANUFACTURING EXAMPLES 4 TO 6

General Manufacturing Procedure 2

6.72 ml of monomer solution 1 per reaction vessel were treated with 0.21 ml of initiator solution 2 in an Accelerator™ SLT100 synthesis reactor from Chemspeed®. Subsequently, the contents were heated at 95° C. for 4 h with shaking, before adding an additional 0.07 ml of initiator solution 2, and the polymerization was brought to completion in 2 h at 95° C.

Manufacturing Example 4

Comb Polymer K4

Monomer solution 1: Mixture consisting of 300 mg of methyl methacrylate, 150 mg of 1-vinyl-2-pyrrolidone and 450 mg of polyethylene glycol methyl ether methacrylate, dissolved in DMF for 8.64 ml.

Initiator solution 2: 100 mg of 2,2'-azobis(2-methylpropionitrile), dissolved in DMF for 1.00 ml.

Manufacturing Example 5

Comb Polymer K5

Monomer solution 1: Mixture consisting of 300 mg of methyl methacrylate, 300 mg of N-vinylcaprolactam and 300 mg of polyethylene glycol methyl ether methacrylate, dissolved in DMF for 8.64 ml.

Initiator solution 2: 100 mg of 2,2'-azobis(2-methylpropionitrile), dissolved in DMF for 1.00 ml.

Manufacturing Example 6

Comb Polymer K6

Monomer solution 1: Mixture consisting of 150 mg of acrylic acid, 450 mg of 2-phenoxyethyl acrylate and 300 mg of polyethylene glycol methyl ether methacrylate, dissolved in DMF for 8.64 ml.

Initiator solution 2: 100 mg of 2,2'-azobis(2-methylpropionitrile), dissolved in DMF for 1.00 ml.

The examples of the comb polymers K7 to K11 compiled in table 1 were obtained using manufacturing procedure 1.

TABLE 1

| Ex. | Monomer Ma | | Monomer Mb | | Monomer Mc | | $M_w$ |
|---|---|---|---|---|---|---|---|
| | Type | Amount | Type | Amount | Type | Amount | |
| K7  | B | 50 | A | 50 | — | — | |
| K8  | B | 67 | A | 33 | — | — | |
| K9  | C | 50 | A | 33 | D | 17 | |
| K10 | B | 50 | A | 33 | D | 17 | |
| K11 | B | 33 | A | 50 | D | 17 | |

The amounts indicated are given in % by weight, based on the total amount of monomers M
A Polyethylene glycol monoethyl ether methacrylate
B Methyl methacrylate
C Butyl acrylate
D Acrylic acid Manufacture of the Active Substance Formulations According to the Invention General Manufacturing Procedure for Solid Active Substance Formulations The active substance or the active substance mixture (total amount 10 g) was dissolved in a solution of the comb polymer according to the invention (30 g) in DMF (70 g). The solvent was removed under vacuum at a temperature of 80° C., a solid homogeneous substance having been obtained which exhibited no crystalline constituents.

The active substance formulations compiled in table 2 were provided using the general preparation procedure.

Leaves of wheat seedlings of the variety "Kanzler" grown in pots were inoculated with a spore suspension of leaf rust (*Puccinia recondita*). The pots were then placed for 24 hours in a chamber with a high air humidity (90 to 95%) at a temperature of 20 to 22° C. During this time, the spores germinated and the germ tubes penetrated into the mesophyll. On the following day, the infected plants were sprayed to runoff point with an aqueous suspension in the active substance concentration given below. The suspension was manufactured as described above. After the spray coating had dried on, the test plants were cultivated for 7 days in a greenhouse at temperatures between 20 and 22° C. and a

TABLE 2

| Example | Active substance 1 | Amount | Active substance 2 | Amount | Polymer | Amount |
|---|---|---|---|---|---|---|
| Z1 | Pyraclostrobin | 15 | Epoxiconazole | 10 | K7 | 75 |
| Z2 | Pyraclostrobin | 15 | Epoxiconazole | 10 | K8 | 75 |
| Z3 | Pyraclostrobin | 15 | Epoxiconazole | 10 | K9 | 75 |
| Z4 | Pyraclostrobin | 15 | Epoxiconazole | 10 | K10 | 75 |
| Z5 | Pyraclostrobin | 15 | Epoxiconazole | 10 | K11 | 75 |
| Z6 | Metconazole | 25 | — | — | K7 | 75 |
| Z7 | Metconazole | 25 | — | — | K8 | 75 |
| Z8 | Metconazole | 25 | — | — | K9 | 75 |
| Z9 | Metconazole | 25 | — | — | K10 | 75 |
| Z10 | Metconazole | 25 | — | — | K11 | 75 |
| Z11 | Epoxiconazole | 25 | — | — | K7 | 75 |
| Z12 | Epoxiconazole | 25 | — | — | K8 | 75 |
| Z13 | Epoxiconazole | 25 | — | — | K9 | 75 |
| Z14 | Epoxiconazole | 25 | — | — | K10 | 75 |
| Z15 | Epoxiconazole | 25 | — | — | K11 | 75 |
| Z16 | Boscalid | 25 | — | — | K7 | 75 |
| Z17 | Boscalid | 25 | — | — | K8 | 75 |
| Z18 | Boscalid | 25 | — | — | K9 | 75 |
| Z19 | Boscalid | 25 | — | — | K10 | 75 |
| Z20 | Boscalid | 25 | — | — | K11 | 75 |
| Z21 | Pyraclostrobin | 15 | Metconazole | 10 | K7 | 75 |
| Z22 | Pyraclostrobin | 15 | Metconazole | 10 | K8 | 75 |
| Z23 | Pyraclostrobin | 15 | Metconazole | 10 | K9 | 75 |
| Z24 | Pyraclostrobin | 15 | Metconazole | 10 | K10 | 75 |
| Z25 | Pyraclostrobin | 15 | Metconazole | 10 | K11 | 75 |
| Z26 | Epoxiconazole | 14 | Metconazole | 11 | K7 | 75 |
| Z27 | Epoxiconazole | 14 | Metconazole | 11 | K8 | 75 |
| Z28 | Epoxiconazole | 14 | Metconazole | 11 | K9 | 75 |
| Z29 | Epoxiconazole | 14 | Metconazole | 11 | K10 | 75 |
| Z30 | Epoxiconazole | 14 | Metconazole | 11 | K11 | 75 |
| Z31 | CMPTP | 25 | — | — | K7 | 75 |
| Z32 | CMPTP | 25 | — | — | K8 | 75 |
| Z33 | CMPTP | 25 | — | — | K9 | 75 |
| Z34 | CMPTP | 25 | — | — | K10 | 75 |
| Z35 | CMPTP | 25 | — | — | K11 | 75 |
| Z36 | CMPTP | 14 | Epoxiconazole | 11 | K7 | 75 |
| Z37 | CMPTP | 14 | Epoxiconazole | 11 | K8 | 75 |
| Z38 | CMPTP | 14 | Epoxiconazole | 11 | K9 | 75 |
| Z39 | CMPTP | 14 | Epoxiconazole | 11 | K10 | 75 |
| Z40 | CMPTP | 14 | Epoxiconazole | 11 | K11 | 75 |

The amounts indicated are given in % by weight, based on the sum of the amounts of active substance and polymer.
CMPTP 5-chloro-6-(2,4,6-trifluorophenyl)-7-(4-methylpiperidin-1-yl)-[1,2,4]triazolo[1,5-a]pyrimidin
Optically water-white solutions were obtained on diluting the formulations Z1 to Z40 with water to an active substance concentration of 64 ppm. The mean particle size of all test specimens was accordingly less than 100 nm.

Performance Trial

Investigation of the Fungicidal Action

The respective active substance formulations were prepared as stock solution with a concentration of active substance of 64 ppm and was subsequently diluted with water to the active substance concentration given below (table 3).

relative humidity of from 65 to 70%. The extent of the development of rust fungi on the leaves was then determined.

The results of the biological trial are combined in table 3. The results show that the active substance mixture stabilized by the comb polymers exhibits, at low application rates, a better fungicidal activity than commercial products.

TABLE 3

| Formulation: Application rate [ppm] | Infection [%] Z1 | Infection [%] Z2 | Infection [%] Z3 | Infection [%] Z4 | Infection [%] Z5 | Infection [%] conv. suspo-emulsion [1] |
|---|---|---|---|---|---|---|
| 63 | 0 | 1 | 0 | 0 | 0 | 3 |
| 32 | 0 | 7 | 4 | 3 | 3 | 17 |
| 16 | 6 | 17 | 10 | 20 | 17 | 50 |

[1] Formulation of the conventional suspoemulsion:
4.7% by weight of epoxiconazole
12.5% by weight of pyraclostrobin
29.2% by weight of aromatic solvents
approx. 12% by weight of fatty alcohol ethoxylate
approx. 4% by weight of phenolsulfonic acid/formaldehyde condensate, sodium salt
Thickener
Biocide
in 1 l of aqueous formulation

We claim:

1. An active substance composition in solid form, comprising:
    i) at least one comb polymer and
    ii) at least one agrochemical active substance, the agrochemical active substance exhibiting a solubility in water at 25° C./1013 mbar of less than 10 g/l, where the comb polymer is obtained by copolymerization of monoethylenically unsaturated monomers M, consisting of:
a) 40 to 85% by weight, based on the total amount of monomers M, of at least one monoethylenically unsaturated monomer Ma chosen from esters of acrylic acids with $C_1$-$C_{20}$-alkanols, esters of acrylic acid with $C_5$-$C_{10}$-cycloalkanols, esters of acrylic acid with phenyl-$C_1$-$C_4$-alkanols, esters of acrylic acid with phenoxy-$C_1$-$C_4$-alkanols, esters of methacrylic acid with $C_1$-$C_{20}$-alkanols, esters of methacrylic acid with $C_5$-$C_{10}$-cycloalkanols, and esters of methacrylic acid with phenyl-$C_1$-$C_4$-alkanols and esters of methacrylic acid with phenoxy-$C_1$-$C_4$-alkanols;
b) 15 to 60% by weight, based on the total amount of monomers M, of at least one monoethylenically unsaturated monomer Mb chosen from the esters of monoethylenically unsaturated $C_3$-$C_8$-monocarboxylic acids and the mono- and diesters of monoethylenically unsaturated $C_4$-$C_8$-dicarboxylic acids with poly($C_2$-$C_4$-alkylene ether)ols that exhibit a number-average molecular weight in the range from 800 to 2000;
c) Up to 20% by weight, monoethylenically unsaturated monomer Mc, which are different from the monomers Ma and Mb, and which are selected from the group consisting of monoethylenically unsaturated $C_3$-$C_8$-monocarboxylic acids and monoethylenically unsaturated $C_4$-$C_8$-dicarboxylic acids;
    the total amount of the monomers Ma and Mb making up at least 80% by weight of the monomers M constituting the comb polymer.

2. The active substance composition of claim 1, wherein at least 50% by weight of the repeat units forming said poly($C_2$-$C_4$-alkylene ether)ols in said comb polymer have the formula $CH_2CH_2O$.

3. The active substance composition of claim 1, wherein said poly($C_2$-$C_4$-alkylene ether)ols in said comb polymer have a molecular weight in the range from 200 to 2000.

4. The active substance composition of claim 1, wherein said poly($C_2$-$C_4$-alkylene ether)ol in said comb polymer is a poly-$C_2$-$C_4$-alkylene glycol mono-$C_1$-$C_{10}$-alkyl ether.

5. The active substance composition of claim 1, wherein said at least one monomer Mb in said comb polymer is selected from the group consisting of esters of monoethylenically unsaturated $C_3$-$C_8$-monocarboxylic acids with poly ($C_2$-$C_4$-alkylene ether)ols.

6. The active substance composition of claim 1, wherein said at least one monomer Mb in said comb polymer is selected from the group consisting of esters of acrylic acid and methacrylic acid with poly($C_2$-$C_4$-alkylene ether)ols.

7. The active substance composition of claim 1, wherein said at least one monomer Ma in said comb polymer is selected from the group consisting of esters of acrylic acid with $C_1$-$C_{10}$-alkanols, and esters of methacrylic acid with $C_1$-$C_{10}$-alkanols.

8. The active substance composition of claim 1, wherein said monomer Mc in said comb polymer comprises 5 to 20% by weight, based on the total amount of the monomers M.

9. The active substance composition of claim 1, wherein said comb polymer has a number-average molecular weight ranging from 2,000 to 500,000 daltons.

10. The active substance composition of claim 1, wherein said comb polymer is present in an amount of 0.3 to 10 parts by weight, based on 1 part by weight of active substance or effect substance.

11. The active substance composition of claim 1, wherein said active substance is selected from the group consisting of fungicidal active substances and insecticidal active substances.

12. The active substance composition of claim 11, wherein said active substance is selected from the group consisting of strobilurins, conazole fungicides, and mixtures thereof.

13. The active substance composition of claim 11, wherein said active substance comprises a mixture of epoxiconazole and at least one additional fungicide selected from the group consisting of metconazole, fluquinconazole and prothioconazole.

14. The active substance composition of claim 1, wherein said active substance comprises a mixture of epoxiconazole and at least one additional fungicide from the group of the strobilurins.

15. The active substance composition of claim 1, wherein the comb polymer is present in the active substance composition in an amount of 0.3 to 10 parts by weight, based on 1 part by weight of the active substance.

16. The active substance composition of claim 1, wherein the proportion of comb polymer in the active substance composition ranges from 20 to 95% by weight, based on the total weight of the composition.

17. The active substance composition of claim 1, wherein the proportion of active substance ranges from 5 to 70% by weight, based on the total weight of the composition.

18. The active substance composition of claim 1, wherein the active substance composition produces, on dilution with water or with an aqueous liquid, an aqueous preparation of the active substance which comprises an aqueous continuous phase and at least one phase comprising the active substance with a mean particle size of not more than 400 nm.

19. The active substance composition of claim 1, wherein said at least one monomer Ma in said comb polymer is selected from the group consisting of esters of acrylic acid with $C_1$-$C_6$-alkanols and esters of methacrylic acid with $C_1$-$C_6$-alkanols.

20. The active substance composition of claim 1, wherein said at least one monomer Ma in said comb polymer is selected from the group consisting of methyl acrylate, methyl methacrylate and butyl acrylate.

21. The active substance composition of claim 1, wherein the monomers Ma comprise at least 80% by weight esters of acrylic acid and methacrylic acid with $C_1$-$C_6$ alkanols, based on the total weight of monomers Ma.

22. The active substance composition of claim 1, wherein the monomers Ma comprise at least 80% by weight methyl acrylate, methyl methacrylate and butyl acrylate, based on the total amount of the monomers Ma.

* * * * *